United States Patent

Goldenberg et al.

(10) Patent No.: US 8,372,019 B2
(45) Date of Patent: Feb. 12, 2013

(54) APPARATUS AND METHOD FOR SENSING FORCE ON A ROBOTICALLY CONTROLLED MEDICAL INSTRUMENT

(75) Inventors: Alex S. Goldenberg, San Francisco, CA (US); Randall L. Schlesinger, San Mateo, CA (US); Eric A. Schultheis, San Jose, CA (US)

(73) Assignee: Hansen Medical, Inc., Mountain View, CA (US)

( * ) Notice: Subject to any disclaimer, the term of this patent is extended or adjusted under 35 U.S.C. 154(b) by 43 days.

(21) Appl. No.: 12/641,145

(22) Filed: Dec. 17, 2009

(65) Prior Publication Data

US 2010/0121269 A1    May 13, 2010

Related U.S. Application Data

(63) Continuation-in-part of application No. 12/269,684, filed on Nov. 12, 2008, now Pat. No. 8,083,691.

(51) Int. Cl.
*A61B 5/103* (2006.01)
*A61B 5/117* (2006.01)

(52) U.S. Cl. ...................................................... 600/587
(58) Field of Classification Search .......... 600/587–595; 606/130
See application file for complete search history.

(56) References Cited

U.S. PATENT DOCUMENTS

| | | | | |
|---|---|---|---|---|
| 5,279,547 | A * | 1/1994 | Costin | 604/22 |
| 5,417,709 | A * | 5/1995 | Slater | 606/205 |
| 5,766,196 | A * | 6/1998 | Griffiths | 606/170 |
| 5,911,694 | A * | 6/1999 | Ikeda et al. | 600/587 |
| 6,068,604 | A * | 5/2000 | Krause et al. | 600/587 |
| 2004/0024402 | A1* | 2/2004 | Nita | 606/45 |
| 2004/0068189 | A1* | 4/2004 | Wilson et al. | 600/459 |
| 2005/0222554 | A1 | 10/2005 | Wallace et al. | |
| 2005/0250989 | A1* | 11/2005 | Suzuki | 600/106 |
| 2005/0273127 | A1* | 12/2005 | Novak et al. | 606/169 |
| 2006/0095022 | A1 | 5/2006 | Moll et al. | |
| 2006/0276775 | A1 | 12/2006 | Rosenberg et al. | |
| 2007/0043338 | A1 | 2/2007 | Moll et al. | |
| 2007/0156123 | A1 | 7/2007 | Moll et al. | |
| 2007/0181139 | A1* | 8/2007 | Hauck | 128/899 |
| 2007/0197896 | A1 | 8/2007 | Moll et al. | |
| 2007/0233044 | A1 | 10/2007 | Wallace et al. | |
| 2010/0057097 | A1* | 3/2010 | Ma et al. | 606/128 |

FOREIGN PATENT DOCUMENTS

EP    1285634 A1 *  2/2003

* cited by examiner

*Primary Examiner* — Rene Towa
(74) *Attorney, Agent, or Firm* — Vista IP Law Group LLP

(57) ABSTRACT

A medical system comprises a medical probe including an elongated probe body, a lumen extending within the probe body, an axially flexible section, and a push-pull member slidably disposed within the lumen. The system comprises a ditherer mechanically coupled to the member for cyclically displacing it axially back and forth within the lumen, such that the ends of the probe body are axially displaced relative to each other via the axially flexible section. The system further comprises a sensor for sensing a force axially applied to the distal end of the probe body. A method comprises introducing a medical probe into a patient, axially dithering the distal end of the medical probe back and forth relative to the proximal end of the medical probe, and sensing a force applied between tissue of the patient and the distal end of the medical probe while the distal end is axially dithered.

5 Claims, 13 Drawing Sheets

APPARATUS AND METHOD FOR SENSING FORCE ON A ROBOTICALLY CONTROLLED MEDICAL INSTRUMENT

RELATED APPLICATION DATA

This application is a continuation-in-part of co-pending U.S. patent application Ser. No. 12/269,684, filed Nov. 12, 2008, which is incorporated by reference into the present application in its entirety.

FIELD OF INVENTION

The inventions disclosed herein relate generally to minimally-invasive medical instruments and systems, such as manually or robotically steerable catheter systems, and more particularly to steerable catheter systems having tissue contact force sensing capability, and their use for performing minimally invasive diagnostic and therapeutic procedures in a human or other animal body.

BACKGROUND

Minimally invasive procedures are preferred over conventional techniques wherein the patient's body cavity is opened to permit the surgeon's hands access to internal organs. Thus, there is a need for highly controllable, yet minimally sized, medical instruments to facilitate imaging, diagnosis and treatment of tissues which may lie deep within a patient, and which may be accessed via naturally-occurring pathways, such as blood vessels, other body passages or lumens, via surgically-created wounds of minimized size, or through combinations thereof.

Currently known minimally invasive procedures for the treatment of cardiac and other disease conditions employ both manually and robotically controlled instruments, such as steerable catheters, which may be inserted transcutaneously into body spaces such as the thorax or peritoneum, transcutaneously or percutaneously into lumens such as the blood vessels, through natural orifices and/or lumens such as the mouth and/or upper gastrointestinal tract, etc. Such devices are well suited for performing a variety of minimally invasive diagnostic and therapeutic procedures.

When manually controlling an elongate instrument, such as a steerable catheter having a proximal end handle, the physician operator (while grasping the handle) can axially push on the proximal end of the catheter and attempt to tactilely "feel" the catheter distal end make contact with pertinent tissue structures located deep in the patient's body, such as the walls of the heart. Some experienced physicians attempt to mentally determine or gauge the approximate force being applied to the distal end of a catheter due to contact with tissue structures or other objects, by interpreting the loads they tactilely sense at the proximal end of the inserted catheter with their fingers and/or hands. Such an estimation of the force, however, is quite challenging given the generally compliant nature of many minimally-invasive instruments, associated frictional loads, dynamic positioning of the instrument versus nearby tissue structures, and other factors.

Robotically controlled catheters have a proximal interface coupled with an instrument driver comprising, for example, one or more motors that are selectively actuated to induce intra-body navigation of the distal portion of the catheter in response to commands input by an operator at a master input station or using some other device that may be located remotely from the patient. Thus, even the most gifted of operator physicians would be unable to gauge forces applied to the distal end of the catheter through tactile feel at the proximal end.

Regardless of the manual or electromechanical nature of the driving mechanism for a diagnostic or interventional catheter, the operator performing the procedure would prefer to have accurate, timely information regarding the forces experienced at the distal portion of the catheter, such as loads applied by or to the catheter from adjacent tissues and other objects.

SUMMARY OF THE INVENTION

In accordance with one embodiment of the disclosed inventions, a medical instrument system comprises a medical probe, a dithering mechanism fixed relative to the probe (e.g., mounted on or in a handle of the probe, or on an instrument driver to which the probe may be operatively coupled), wherein the dithering mechanism mechanically actuates a push-pull member extending axially through the probe for causing a distal tip of the probe to dither (i.e., move back and forth) axially relative to a more proximal portion of the probe, and at least one force sensor located at a proximal end portion of the push-pull member and configured to sense forces applied on or by (collectively "to") the push-pull member and, thus, the distal tip of the probe.

More particularly, the medical probe has an elongated probe body (e.g., a flexible intravascular catheter body) having a distal tip section, a bendable section located proximally to the distal tip section, and an axially variable-length (e.g., an axially compressible or translatable) section interposed between the bendable and distal tip sections. In one embodiment, the axially variable-length section of the probe body comprises an axially compressible polymer sleeve. In another embodiment, the axially variable-length section of the probe body comprises a bellows. In still another embodiment, the axially variable-length section of the probe body comprises at least one seal that allows one of the bendable and distal tip sections of the probe body to slide axially within the other. The medical probe may further include one or more operative elements, such as tissue sensing, pacing and/or ablation electrodes, mounted to the distal tip section.

One or more steering control elements (e.g., wires) extend through the probe body for deflecting the distal tip section in at least one direction. The distal ends of the control element(s) are preferably affixed to the probe body at a location proximal of the axially variable-length section. In one exemplary embodiment, the probe body has four control elements circumferentially spaced 90 degrees apart and extending from a proximal end portion of the probe body to a steering anchor ring fixed at a distal end of the bendable section. If the probe is manually controlled, the proximal end of the probe body will include a handle having one or more steering mechanisms therein for manipulating the control elements in order to controllably deflect the bendable section of the probe. If the probe is robotically controlled, the control elements are coupled with respective motors in an instrument driver to which the probe is operatively mounted in order to controllably deflect the bendable section of the probe.

The push-pull member may comprise one or more relatively stiff wires, and is slidably disposed through an axially extending lumen of the probe, with a distal end of the push-pull member being affixed to the distal tip section of the probe body, and with a proximal end of the push-pull member extending out of an opening in the proximal end of the probe body for coupling to the dithering mechanism. In particular, the push-pull member (and, thus, the distal tip section of the probe body) is axially displaced by the dithering mechanism relative to the respective handle or instrument driver, and also relative to the steering control elements which terminate in the probe body proximally of the axially variable-length section.

In one embodiment, the medical probe further comprises a substantially incompressible stiffening coil that extends axially through the inner lumen of the probe, the push-pull member extending through a center of, and being translatable relative to, the stiffening coil, with the coefficient of friction between the outer surface of the stiffening coil and the inner surface of the probe body defining the lumen being minimized. In one embodiment, the stiffening coil is affixed to the probe body at a steering wire anchor member located at a distal end of the bendable section. In another embodiment, a distal end portion of the stiffening coil extends past the steering wire anchor member and through the axially variable-length section before terminating against the distal tip section. The pitch of the individual coil windings in this distal portion of the stiffening coil is significantly opened, and the diameter of the individual windings is substantially expanded, so that the coil portion extending past the anchor member functions as a resilient tensioning spring to help maintain the push-pull member in tension as the push-pull member is dithered back and forth through the probe body lumen.

The dithering mechanism mechanically couples with (e.g., "grasps") a proximal end portion of the push-pull member extending out of a proximal end of the probe body, and is configured for cyclically displacing the push-pull member axially back and forth within the lumen of the probe body, such that the respective bendable and distal tip sections of the probe body are axially displaced relative to each other via the axially variable-length section disposed therebetween. One or more force (or load) sensors are mounted to the dithering mechanism or at some other location that is fixed with respect to the motion of the push-pull member. In particular, the force sensor(s) are arranged and configured for measuring an axial force (or "load") on the push-pull member, which includes any external force axially applied to the distal tip of the probe body.

The medical instrument system further comprises a computer (more generically, a "processor") programmed for obtaining a "baseline" force measurement based on signals received from the force sensor(s) when the push-pull member is dithered back and forth without any external axial force applied to the distal tip of the probe body (a condition determined by the system operator, e.g., during a system initiation process). Thereafter, a "total" force measurement is obtained based on signals received from the force sensor(s) when the push-pull member is dithered back and forth when external axial forces are being applied to the distal tip of the probe body. The net external axial force applied to the distal tip of the probe body is then calculated by the processor by subtracting the baseline force measurement from the total force measurement.

In one embodiment, the axially variable-length section of the probe body is a compressible polymer sleeve with a spring member axially disposed therein to maintain tension on the push-pull member during the dithering operation. In particular, a proximal end of the spring is compressible against a distal-facing surface of a steering element anchor ring that also defines a distal end of the bendable section, and a distal end of the spring is compressible against a proximal-facing surface of the probe distal tip section.

Prior to attachment of the push-pull member to the dithering mechanism, the tensioning spring is preferably in an unloaded state. When initiating the instrument system for performing a procedure in a patient, the proximal end portion push pull member is retracted proximally relative to the distal tip section of the probe body, thereby retracting the distal tip section relative to the bendable section, and compressing the spring against the anchor ring. Once a specified load on the push-pull member (as measured by the force sensor(s)) is reached, the proximal end portion of the push-pull member is affixed to the dithering mechanism, and dithering of the push-pull member is commenced, with a back-and-forth stroke distance traveled by the push-pull member governed by maintaining the measured (or "sensed") load on the push-pull member within a specified operating range.

As the dithering mechanism "pushes" the push-pull member (and, thus, the distal tip section of the probe) in a distal direction axially relative to the handle or instrument driver on which the dithering mechanism is mounted, the spring decompresses, thereby decreasing the measured load on the push-pull member until the lower end of the operating load range is reached, which is preferably at a point when the spring returns to a slightly pre-loaded state but without allowing the spring to being axially tensioned. Preferably, there is always at least some pre-load in the spring, i.e., the spring is not allowed to return to a fully unloaded position. It is also preferable that the spring is never placed in a fully compressed condition.

Thereafter, the dithering mechanism reverses direction and "pulls" the push-pull member (and, thus, the distal tip section of the probe) in a proximal direction axially relative to the handle or instrument driver on which the dithering mechanism is mounted, and the spring is again compressed (but not fully) against the anchor ring, resisting the inward motion of the probe distal tip and increasing the measured load on the push-pull member until the upper end of the load range is reached. The dithering cycle is then repeated.

In some embodiments, the medical probe may comprise a fluid delivery tube extending axially through the inner probe lumen for delivering cooling fluid, e.g., saline from a fluid supply port located at a proximal end of the probe to the distal tip of the probe. The cooling fluid may be circulated within an interior region of the tip and returned to the proximal end of the probe (and out a fluid outlet port) through an additional fluid return tube. Alternatively, the fluid may be released into the patient's body through one or more fluid outlet passages formed in the probe distal tip. Either way, in accordance with certain embodiments of the disclosed inventions, the fluid delivery tube may also be used as the push-pull member for dithering the distal tip section of the probe relative to the bendable section. In such embodiments, a proximal portion of the fluid delivery tube extending out of the proximal end of the probe is mechanically coupled to the dithering mechanism in the same manner as the above-described push-pull member.

In accordance with another aspect of the present inventions, a medical method is provided, the method comprising introducing a medical probe having an elongated probe body into a patient (e.g., intravascularly), axially dithering the distal end of the probe body back and forth relative to a more proximal portion of the probe body, and sensing a force applied between tissue of the patient and the distal end of the probe body while the distal end of the probe body is being axially dithered. In embodiments of the method, the force applied between the tissue and the distal end of the probe body is determined by first obtaining a baseline force measurement when the distal end of the probe body is axially dithered back and forth without an external axial force axially applied between the tissue and the distal end of the probe body, subsequently obtaining a total force measurement when the distal end of the probe body is dithered at the same time an external axial force is axially applied between the tissue and the distal end of the probe body, and then subtracting the baseline force measurement from the total force measurement.

Other and further aspects and features of the disclosed inventions will be evident from reading the following detailed description of the preferred embodiments, which are intended to illustrate, not limit, the disclosed inventions.

BRIEF DESCRIPTION OF THE DRAWINGS

The drawings illustrate the design and utility of various embodiments of the disclosed inventions, in which similar elements are referred to by common reference numerals. In order to better appreciate how the above-recited and other advantages and objects of the disclosed inventions are obtained, a more particular description of the disclosed inventions described above is provided herein by reference to specific embodiments thereof, which are illustrated in the accompanying drawings. Understanding that these drawings depict only some of the possible embodiments of the invention and are not therefore to be considered limiting of its scope, the disclosed inventions are described and explained herein with additional specificity and detail through the use of the accompanying drawings, in which.

DETAILED DESCRIPTION OF THE ILLUSTRATED EMBODIMENTS

Figure 1:
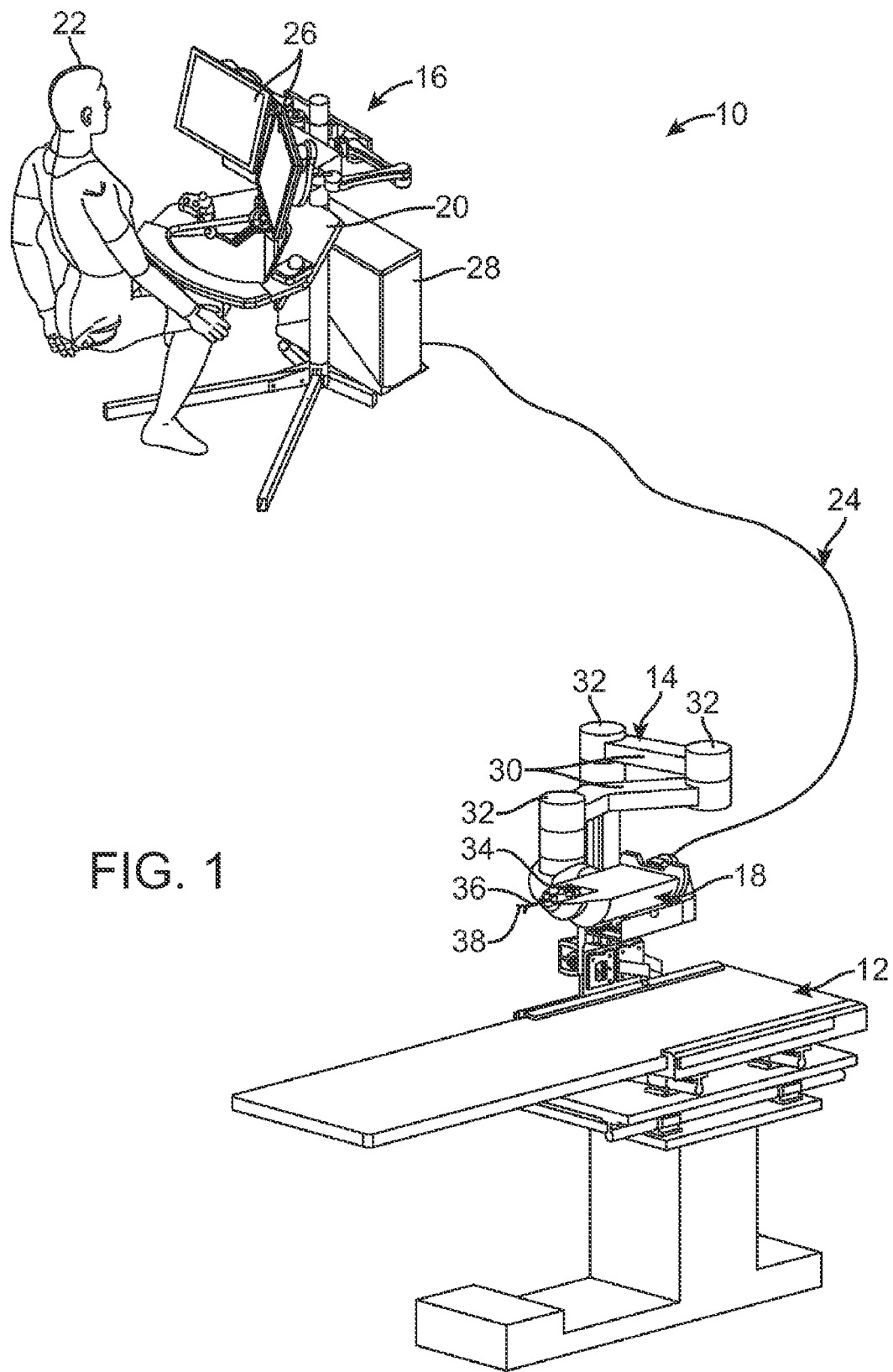
FIG. 1 is a perspective view of a robotically controlled medical instrument system constructed in accordance with one embodiment of the disclosed inventions.

Before describing the specific illustrated embodiments in detail, it is to be understood that, unless otherwise indicated, the inventions disclosed herein need not be limited to applications in humans. As one of ordinary skill in the art would appreciate, variations of the invention may be applied to other mammals as well. Moreover, it should be understood that embodiments of the disclosed inventions may be applied in combination with various catheters, introducers, or other surgical tools for performing minimally invasive surgical procedures.

As used in this specification and the appended claims, the singular forms "a," "an" and "the" include plural referents unless the context clearly dictates otherwise. Thus, for example, the term "a member" is intended to mean a single member or a combination of joined or separate members, "a fluid" is intended to mean one or more fluids, or a mixture thereof. Furthermore, the words "proximal" and "distal" refer to direction close to and away from, respectively, an operator (e.g., surgeon, physician, nurse, technician, etc.) who would insert the medical device into the patient, with the tip-end (i.e., distal end) of the device inserted inside a patient's body first. Thus, for example, the catheter end inserted inside the patient's body would be the distal end of the catheter, while the catheter end left outside the patient's body would be the proximal end of the catheter.

Before describing an embodiment of a robotic catheter system constructed in accordance with the disclosed inventions, it may be helpful to first describe one robotic catheter system that has been previously designed to sense force. U.S. patent application Ser. No. 11/678,001 (the '001 application), which is commonly assigned with the present application, discloses robotically-navigated interventional systems and methods having the capability to sense force between a distal end of a working instrument (such as a catheter) and the surface of a body cavity or lumen (referred to collectively as a "body space"). The robotic system of the '001 application not only detects contact between the working instrument and the surface, but also measures the magnitude of the force, also called the load. Such systems and methods can also be used to detect contact with tissue structures.

In particular, the robotic system described in the '001 application comprises a robotic instrument driver that directly interfaces with a coaxial arrangement of an introducer sheath and a guide catheter, and an operator control station for remotely controlling movements of the introducer sheath and guide catheter through the instrument driver. A working instrument, e.g., a cardiac mapping or ablation catheter which can be manually operated by a physician, is disposed through the robotically controlled guide catheter via a hemostatic (e.g., Touhy) valve. The guide catheter, in turn, is disposed through the robotically controlled introducer sheath. The instrument driver comprises separate instrument interfaces for coupling to respective instrument driver adapters (sometimes referred to as "splayers") attached at proximal base portions of the sheath and catheter in a manner providing for controlled manipulation of respective steering control elements (wires) extending through the sheath and catheter to provide them with independent steering actuation. The instrument driver may also move the instrument interfaces and, thus, the respective introducer sheath and guide catheter splayers relative to each other to provide independent axial insertion or retraction movements to the introducer sheath and guide catheter along a longitudinal axis.

The robotic system described in the '001 application measures a force applied on a distal end of the working instrument using a dithering technique. In particular, the working instrument is "dithered" with respect to the guide catheter through which it extends by moving (i.e., axially translating) the working instrument back and forth relative to the guide catheter in a repeated cyclic motion to overcome frictional challenges that would otherwise complicate measuring loads at the instrument's distal end. That is, if the working instrument is positioned down the lumen of the guide catheter so that the distal end of the working instrument extends out slightly beyond (and out of) the open distal end of the guide catheter, it may be difficult to accurately sense forces applied to the distal end of the working instrument due to the frictional complications of the physical relationship between the working instrument and guide catheter. In a steady state wherein there is little or no relative axial or rotational motion between the working instrument and the guide catheter, the static coefficient of friction is applicable and, as such, there are relatively large frictional forces keeping the working instrument in place relative to the guide catheter such that there is no relative movement between the two when measured at the proximal end of the working instrument after the various frictional losses are absorbed along its length. To release this relatively tight coupling and facilitate an accurate measurement of forces applied to the distal end of the working instrument, the dithering motion is used to effectively break loose this frictional coupling with the guide catheter.

The dithering motion is provided by a "ditherer" (more generically, "dithering mechanism") that is mechanically coupled to the proximal end portion of the working instrument extending out from the proximal end of the guide catheter. A bellows is provided on the hemostatic valve through which the working instrument is inserted into the guide catheter to allow for dithering of the working instrument, while preventing fluid(s) from exiting the guide catheter. One or more sensors are provided on (or adjacent to) the ditherer for measuring forces applied at the distal end of the working instrument and transmitted through its shaft to the ditherer. The sensor(s) are operatively coupled to a controller that determines a baseline dynamic frictional force between the working instrument and guide catheter based on output signals from the sensor(s) that represent the respective insertion and withdrawal forces generated by the moving working instrument relative to the guide catheter at a time when no external forces are exerted on the working instrument. Thus, any additional forces applied to the distal end of the working instrument can be calculated by the controller by subtracting the baseline frictional force from the total measured force.

Thus, the specific dithering techniques taught and discussed in the '001 application provides an accurate technique for sensing forces applied to the distal end of a manually operated working instrument extending through (and out the distal end of) a robotically controlled guide catheter. The contents of the '001 application are incorporated herein by reference. The embodiments disclosed herein are directed to the use of dithering systems and techniques for sensing forces applied to the distal end of an "all-in-one" instrument that may be a manually controlled instrument having a proximal handle, or a robotically controlled instrument (e.g., a robotically steerable catheter having a therapeutic and/or diagnostic function), despite the fact that the proximal end of the instrument is affixed to a robotically controlled instrument driver.

Referring to FIG. 1, one embodiment of a robotically controlled catheter system 10 constructed in accordance with the disclosed inventions will now be described. The system 10 generally comprises an operating table 12 having a movable support-arm assembly 14, an operator control station 16 located remotely from the operating table 12, and a robotic catheter assembly 18 mounted to the support-arm assembly 14 above the operating table 12. In addition to the systems disclosed in the above-incorporated '001 application, exemplary robotic catheter systems that may be modified for constructing and using embodiments of the inventions disclosed herein are described in detail in the following U.S. patent applications, which are all expressly incorporated herein by reference in their entirety: U.S. patent application Ser. No. 11/073,363, filed Mar. 4, 2005; U.S. patent application Ser. No. 11/179,007, filed Jul. 6, 2005; U.S. patent application Ser. No. 11/418,398, filed May 3, 2006; U.S. patent application Ser. No. 11/481,433, filed Jul. 3, 2006; U.S. patent application Ser. No. 11/637,951, filed Dec. 11, 2006; U.S. patent application Ser. No. 11/640,099, filed Dec. 14, 2006; U.S. Patent Application Ser. No. 60/833,624, filed Jul. 26, 2006; and U.S. Patent Application Ser. No. 60/835,592, filed Aug. 3, 2006.

The control station 16 comprises a user interface 20 that is operatively connected to the robotic catheter assembly 18. A physician or other operator 22 may interact with the user interface 20 to operate the robotic catheter assembly 18. The user interface 20 is connected to the robotic catheter assembly 18 via a cable 24 or the like, thereby providing one or more communication links capable of transferring signals between the control station 16 and the robotic catheter assembly 18. Alternatively, the user interface 20 may be located in a geographically remote location and communication is accomplished, at least in part, over a wide area network such as the Internet. The user interface 20 may also be connected to the robotic catheter assembly 18 via a local area network or even wireless network that is not located at a geographically remote location.

The control station 16 also comprises one or more monitors 26 used to display various aspects of the robotic instrument system 10. For example, one or more images of the introducer sheath and working catheter of the robotic catheter assembly 18 (described in further detail below) may be displayed in real time on the monitors 26 to provide the physician 22 with the current orientation of the various devices as they are positioned, for example, within a body lumen or region of interest. The control station 16 further comprises a computer 28, which may comprise a personal computer or other type of computer work station, for performing the data processing operations disclosed herein.

The support-arm assembly 14 is configured for movably supporting the robotic catheter assembly 18 above the operating table 12 to provide convenient access to the desired portions of the patient (not shown), and also to provide a means to lock the catheter assembly 18 into position subsequent to the preferred placement. In one embodiment, the support-arm assembly 14 comprises a series of rigid links 30 coupled by electronically braked joints 32, which prevent joint motion when unpowered, and allow joint motion when energized by the control station 16. In an alternative embodiment, the rigid links 30 may be coupled by more conventional mechanically lockable joints, which may be locked and unlocked manually using, for example, locking pins, screws, or clamps. The rigid links 30 preferably comprise a light but strong material, such as high-gage aluminum, shaped to withstand the stresses and strains associated with precisely maintaining three-dimensional position of the weight of the catheter assembly 18.

Figure 2:
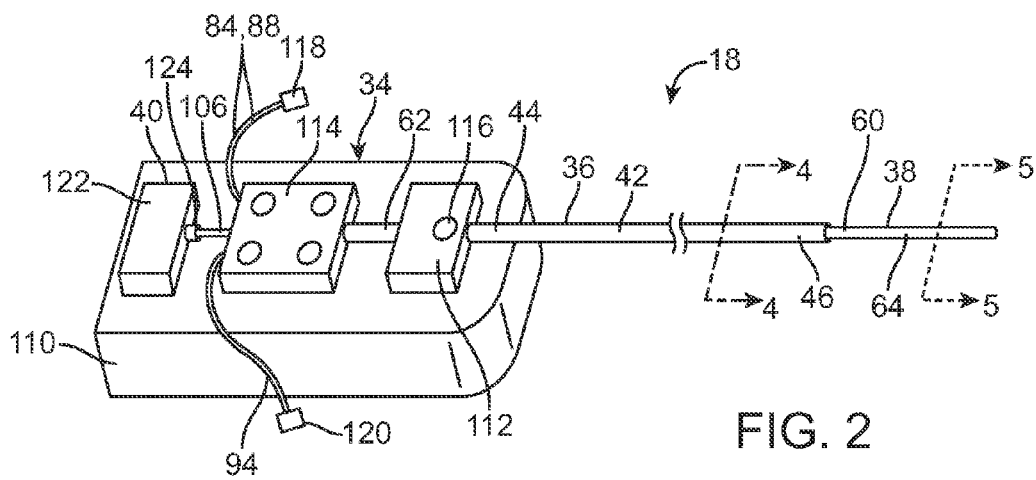
FIG. 2 is a perspective view of a robotically controlled catheter instrument assembly that may be employed in the medical robotic system of FIG. 1.
Figure 3:
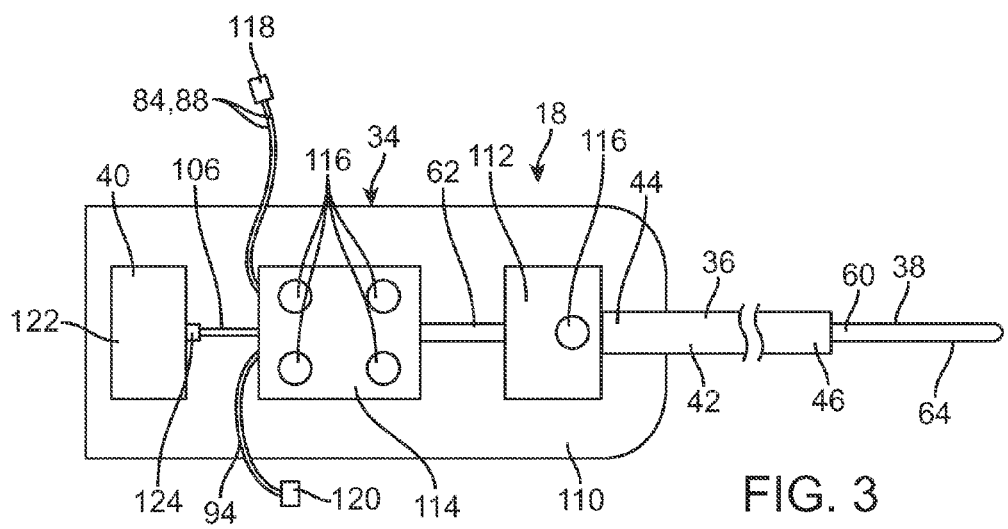
FIG. 3 is a top view of the robotic catheter assembly of FIG. 2.

Referring further to FIGS. 2 and 3, the robotic catheter assembly 18 will now be described in greater detail. The catheter assembly 18 generally comprises a remotely controlled instrument driver 34, with a robotic introducer sheath 36 and a robotically controlled working catheter 38 mounted to the instrument driver 34 in a coaxial relationship, i.e., with the working catheter 38 extending coaxially through a lumen of the introducer sheath 36. A dithering force sensing assembly 40 is mounted to the instrument driver 16 in mechanical communication with a push-pull member 106 (e.g., comprising one or more wires) extending from the open proximal end of the working catheter 38, as described in greater detail herein. The robotic catheter assembly 18 may also include a sterile drape (not shown) that covers the instrument driver 34.

Figure 4:
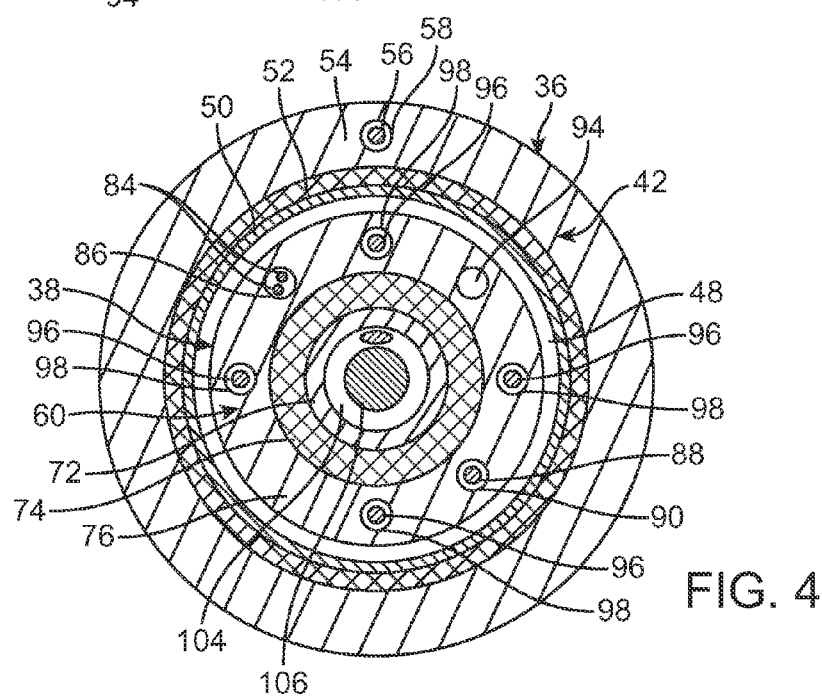
FIG. 4 is a cross-sectional view of a respective introducer sheath and working catheter used in the robotic catheter assembly of FIG. 2, particularly taken along the line 4-4.

Referring also to FIG. 4, the introducer sheath 36 comprises an elongated sheath body 42 having a proximal end 44, a distal end 46, and a working lumen 48 extending through the sheath body 42 between the proximal and distal ends 44, 46. It will be appreciated that the geometry and size of the sheath working lumen 48 is selected in accordance with the corresponding cross-sectional geometry and size of the working catheter 38. The sheath body 42 preferably has a low-friction inner surface or layer 50, e.g., a coating of silicone or polytetrafluoroethylene, to provide a low-friction surface to accommodate movement of the working catheter 38 within the working lumen 48, with a stiffening layer 52 (e.g., a braided material or a metallic spine) disposed over the outer surface of the inner layer 50, and an outer polymer jacket 54 disposed over the outer surface of the stiffening layer 52.

The introducer sheath 36 further comprises a control element in the form of steering wire 56 extending through a steering lumen 58 disposed within the wall of the sheath body 42, and in particular, extending through the polymer jacket 54. The distal end of the steering wire 56 is suitably mounted to an anchoring element, e.g., an annular ring (not shown), located at the distal end 46 of the sheath body 42, and the proximal end of the steering wire 56 extends out the proximal end 44 of the sheath body 42, so that it can be suitably coupled to instrument driver 34, via an introducer sheath splayer 112, as discussed below. Thus, it can be appreciated that the distal end 44 of the sheath body 42 can be alternately deflected and straightened via actuation of the steering wire 56 by a motor in the instrument driver 34 coupled to the steering wire via the sheath splayer 112. In alternate embodiments, the introducer sheath 36 may be provided with one or more additional steering wires controlled by respective motors in the instrument driver 34, via the sheath splayer 112, to provide for increased distal bending capability.

The working catheter 38 is an exemplary embodiment of an elongate probe instrument of the presently disclosed inventions, and may take the form of any number of types of catheters. In the illustrated embodiment, the working catheter 38 takes the form of an electrophysiology/ablation catheter, wherein forces imposed between the distal end of the working catheter 38 can be communicated to an ablation energy generator (not shown) as an input parameter. For example, the ablation energy generator may be prevented from operation unless the sensed force on the distal end of the working catheter is within a range that confirms there is adequate tissue contact required to provide effective treatment. By way of another example (not mutually exclusive of the prior example), the ablation energy generator may automatically compute and set and particular ablation power, ablation time, temperature, etc., as a function of the sensed force at the distal end of the working catheter. It should be noted that the working catheter 38 may alternatively or additionally carry other types of operative elements, such as a tissue manipulation tool or other device, also called "end effectors", such as e.g., an imaging device or cutting tool disposed on the distal end of the catheter 38. It should also be noted that, although the working catheter 38 is described as an intravascular catheter, other types of medical probes may be used. For example, the working catheter 38 may take the form of an endoscopic surgical instrument or other elongated medical instrument. Depending on the application, the working catheter 38 can be rigid or semi-rigid.

The working catheter 38 passes through the lumen 48 of the introducer sheath 36, and is axially and rotatably moveable relative thereto. As shown in FIGS. 2 and 3, the working catheter 38 may project distally out the open distal end 44 of the introducer sheath body 42, although the working catheter 38 may also be withdrawn proximally such that its distal end is substantially flush with the distal end 44 of the sheath body 42, or withdrawn even further such that its distal end is disposed completely within the sheath body 42. The working catheter 38 may be movably positioned within the working lumen 48 of the introducer sheath 36 to enable relative insertion of the two devices, relative rotation (or "roll") of the two devices, and relative steering or bending of the two devices, particularly when the distal end of the working catheter 38 is inserted into a patient's body beyond the open distal end 44 of the introducer sheath 36.

Figure 6:
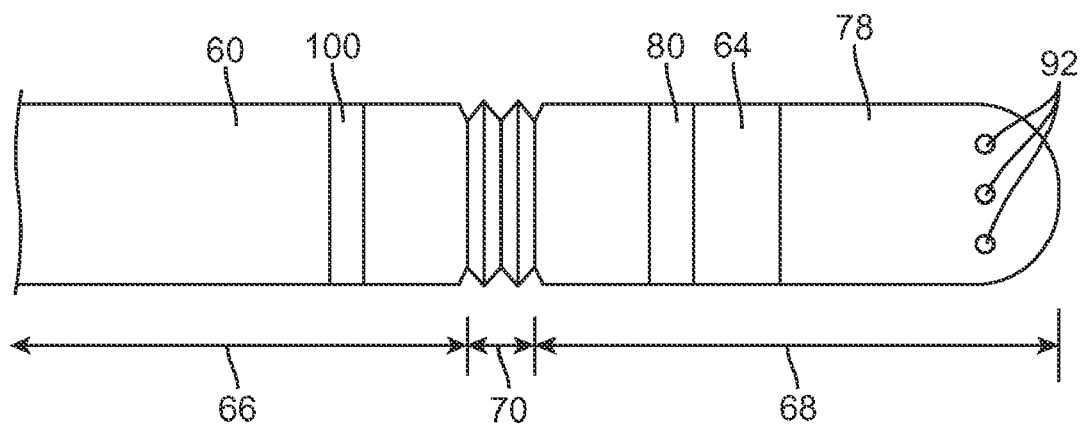
FIG. 6 is a plan view of the distal end of the working catheter used in the robotic catheter assembly of FIG. 2.
Figure 7:
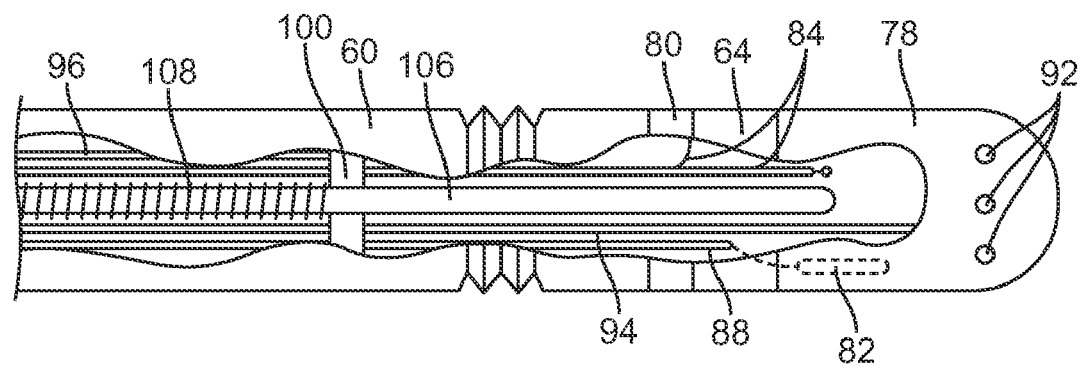
FIG. 7 is a partially cut-away view of the distal end of the working catheter used in the robotic catheter assembly of FIG. 2.

Referring additionally to FIGS. 6 and 7, the working catheter 38 comprises an elongated catheter body 60 having a proximal end 62 and a distal end 64. With respect to its composition, the catheter body 60 can be generally divided into three sections: a bendable shaft section 66, a distal tip section 68, and an axially compressible section 70 disposed between the respective bendable and distal tip sections 66, 68. The term "axially compressible," as used herein, means that the respective catheter section is more compressible than the adjoining bendable and distal tip sections 66, 68. As such, when an axial force is placed on the distal tip section 68 by the push-pull member 106 (or by an external force), the tip section 68 moves axially relative to the bendable section 66, with the resulting compression or tension forces being absorbed by the axially compressible section 70, with the bendable and tip sections 66, 68 being relatively axially incompressible.

Figure 5:
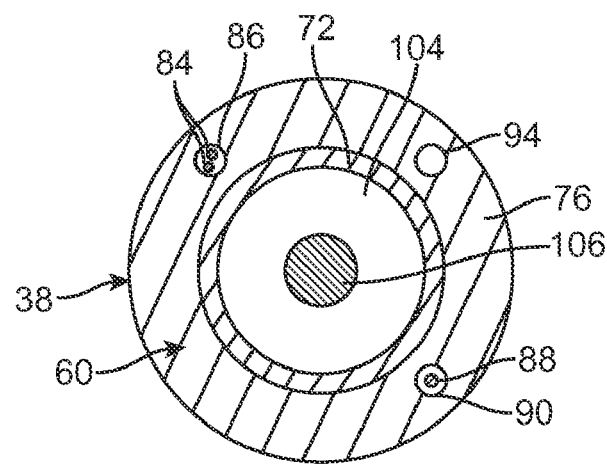
FIG. 5 is a cross-sectional view of the working catheter used in the robotic catheter assembly of FIG. 2, particularly taken along the line 4-4.

As best shown in FIG. 4, the bendable section 66 of the catheter body 60 may be composed of a low-friction inner lubricious layer 72, a stiffening layer 74 (e.g., a braided material or a metallic spine) disposed over the outer surface of the inner layer 72, and an outer polymer jacket 76 disposed over the outer surface of the stiffening layer 74. Because the bendable section 66 is structurally reinforced by inclusion of the stiffening layer 74, torque transmission and insertability of the catheter 38 is enhanced, while also providing enough cantilever bendability to facilitate access to remote tissue locations, such as the chambers of the heart. As best shown in FIG. 5, the distal tip section 68 of the catheter body 60 is composed of the inner lubricious layer 72 and the polymer jacket layer 76, and is more laterally flexible than the proximal section 66 due to the lack of a stiffening layer.

Significantly, the axially compressible section 70 of the catheter body 60, which in the illustrated embodiment in FIGS. 6 and 7 takes the form of a bellows, can axially elongate and contract in much the same way as an accordion, thereby allowing the distal tip section 68 to be axially displaced relative to the bendable section 66 in response to the application of an axial (tension or compression) force exerted on the distal tip section 68. As will be described in further detail below, this feature allows the distal end 64 of the catheter body 60 to be axially dithered back and forth, while also facilitating the transfer of axial forces externally applied to the distal end 64 of the catheter body 60 to the force sensing assembly 40.

As briefly discussed above, the working catheter 38 takes the form of an electrophysiology/ablation catheter, and thus, comprises an ablation electrode, and in particular, a tip electrode 78, and an electrophysiology mapping electrode, and in particular, a ring electrode 80 mounted around the distal end 64 of the catheter body 60 proximal to the tip electrode 78. The electrodes 78, 80 may be composed of a suitably electrically conductive material, such as stainless steel or platinum. The catheter may further comprise a temperature sensor 82 (shown in phantom), such as a thermocouple or thermistor, suitably mounted within the tip electrode 78.

The working catheter 38 comprises electrical leads 84 extending through a wire lumen 86 (shown in FIGS. 4 and 5) within the catheter body 60, with the distal ends of the electrical leads 84 respectively terminating at the tip electrode 78 and ring electrode 80, and the proximal ends of the electrical leads 84 terminating in the instrument driver 34 (described in further detail below). The working catheter 38 also comprises an electrical lead 88 extending through a wire lumen 90 (shown in FIGS. 4 and 5) within the catheter body 60, with the distal end of the electrical lead 88 terminating at the temperature sensor 82, and the proximal end of the electrical lead 88 terminating in the instrument driver 34 (described in further detail below).

The tip electrode 78 optionally includes fluid irrigation ports 92 through which a cooling fluid, such as saline, can flow into the patient's body. In this case, the catheter 38 comprises a fluid supply tube 94 extending through the catheter body 60, with a distal end of the fluid supply tube 94 terminating within the tip electrode 78 in fluid communication with the irrigation ports 92, and a proximal end of the fluid supply tube 94 terminating at fluid inlet port at the proximal end of the working catheter 36 (described in further detail below).

The working catheter 38 further comprises a plurality of control elements (in this case, four) in the form of steering wires 96 extending through respective steering lumens 98 disposed within the wall of the catheter body 60, and in particular, through the outer polymer jacket layer 76 of the proximal section 66. The working catheter 38 further comprises a steering wire anchoring element in the form of an anchoring ring 100, embedded within the outer polymer jacket layer 76 at the distal end of the bendable section 66 of the catheter body 60. The respective distal ends of the steering wires 96 (only one is shown in FIG. 7) are suitably mounted to the anchoring ring 100, and the respective proximal ends of the steering wires extend out the proximal end 62 of the catheter body 60, for being suitably coupled to instrument driver 34 (described in further detail below). In the illustrated embodiment, the proximal end 62 of the catheter body 60 includes apertures (not shown) through which the respective steering wires 96 exit for coupling to the instrument driver 34. Thus, it can be appreciated that the distal end 64 of catheter body 60 can be alternately deflected in four different directions and straightened via remotely controlled actuation of the steering wires 96.

The working catheter 38 has a central lumen 104 extending axially through the catheter body 60 between the proximal and distal ends 62, 64. The push-pull member 106 is slidably disposed within the central lumen 104, wherein a distal end of the push-pull member 106 extends through the anchor ring 100 and is affixed to the distal tip section 64 (e.g., by soldering it to the inner surface of the tip electrode 78). In one embodiment, the push-pull member 106 is a 0.010" diameter 304SS wire attached to a solid metal electrode 78 forming the distal part of the distal tip section 68 by soldering or laser welding. It will be appreciated that the push-pull member 106 should extend along the neutral (central) of the catheter body 60 to reduce and (if possible) eliminate the need for any geometric compensation.

A proximal end of the push-pull member 106 extends out from the proximal end 62 of the catheter body 60, so that it can be suitably coupled to the force sensing assembly 40, as will be described in further detail below. In one embodiment, the push-pull member 106 may also function as a "safety wire" to protect the patient if the distal tip section 68 of the catheter body 60 should somehow separate from the compressible section 70. The push-pull member 106 may also be used as an electrical lead 84 in lieu of one of the electrical leads 84 discussed above. In this case, the push-pull member 106 preferably includes an electrically conductive core and an electrically insulative coating disposed over the core.

The working catheter 38 optionally comprises a stiffening coil 108 that also extends axially through its central lumen 104, with the push-pull member 106 extending through a center of, and being axially translatable relative to, the stiffening coil 108. The stiffening coil 108 may be composed of a material or be coated with a material that has a lower coefficient of friction than that of the push-pull member 106. For example, the stiffening coil 108 may be coated with polytetrafluoroethylene. In this manner, friction between the push-pull member 106 and the inside surface of the stiffening coil 108 is preferably minimized, as such friction may otherwise be excessive if too much surface area of the push-pull member 106 is in contact with the inside surface of the stiffening coil 108 when the bendable shaft section 66 of the working catheter 38 is articulated in response to actuation of one of the steering wires 96. The coil 108 also facilitates the centering of the push-pull member 106 within the central lumen 104 of the catheter 38.

In an alternate embodiment, depicted in relevant part in below-described FIG. 15a, a distal end portion 111 of the stiffening coil 108 may extend past the steering wire anchor ring 100, and through the axially compressible section 70, before terminating at a proximal end surface 69 of the distal tip section 68. In this distal end portion 111 of the stiffening coil 108, the pitch of the coil windings is significantly opened and their diameters are substantially expanded, so that the distal coil portion 111 functions as a resilient tensioning spring to help maintain the push-pull member 106 (the fluid supply tube 94' in FIG. 15*a*) in tension during the dithering operation.

Referring back to FIGS. 2 and 3, the instrument driver 34 provides robotic steering actuation, as well as robotic insertion and retraction actuation, to the respective introducer sheath 36 and working catheter 38 in accordance with control signals transmitted from the control station 16 (shown in FIG. 1). In particular, the instrument driver 34 comprises a housing 110 that contains motors (not shown), an introducer sheath interface to which the sheath splayer 112 is operatively mounted, and a working catheter interface to which the catheter splayer 114 is operatively mounted.

The respective splayers 112, 114 are mechanically interfaced to the housing 110 in such a manner that they may be axially displaced relative to each other via operation of the motors, thereby effecting insertion or retraction movements of the respective introducer sheath 36 and working catheter 38 relative to each other, and thus, relative to the operating table 12 (shown in FIG. 1). Each of the splayers 112, 114 comprises one or more rotating spools or drums 116 that can selectively tension or release the steering wires 56, 96 disposed within the respective sheath body 42 and catheter body 60, thereby effecting deflection of the distal ends 46, 64 of the sheath and catheter bodies 42, 60. In some embodiments, the instrument driver 34, in conjunction with the support arm 14, may optionally be capable of rotating or rolling the sheath body 42 and catheter body 60 relative to each other. If the working catheter 38 alternatively or additionally includes an operative element requiring mechanical actuation, the instrument drive 34 and/or catheter splayer 114 may include additional spools (not shown) for tensioning control elements (not shown) used for actuating such operative element.

The proximal ends of the electrical wires 84, 88 exit from the proximal end 62 of the catheter body 60 into the catheter splayer 114, which then exit the catheter splayer 114 as a bundle of wires that are terminated in an electrical connector 118. A radio frequency (RF) generator and electrophysiology mapping equipment (both not shown) can be coupled to the electrical connector 118 to allow the transmission of RF energy and temperature signals between the RF generator and the tip electrode 78 and temperature sensor 82 (shown in FIGS. 6 and 7), and to allow the transmission of signals between the ring electrode 80 (shown in FIGS. 6 and 7) and the electrophysiology mapping equipment.

The proximal end of the fluid supply tube 94 exits from the proximal end 62 of the catheter body 60 through the splayer 114, and terminates at a luer connector 120. A fluid pump (not shown) can be coupled to the luer connector 120 to convey pressurized fluid into the fluid supply tube 94 and out through the fluid delivery ports 92 on the tip electrode 78 (shown in FIGS. 6 and 7). In an alternate "closed fluid cooling" embodiment (not shown), fluid from the fluid supply tube 94 circulates within an interior region of the distal tip section 64 and returns to the proximal end of the catheter 38 through an additionally-provided fluid outlet tube. In such alternate embodiment, there are no fluid delivery ports 92 in the tip electrode 78.

Figure 14:
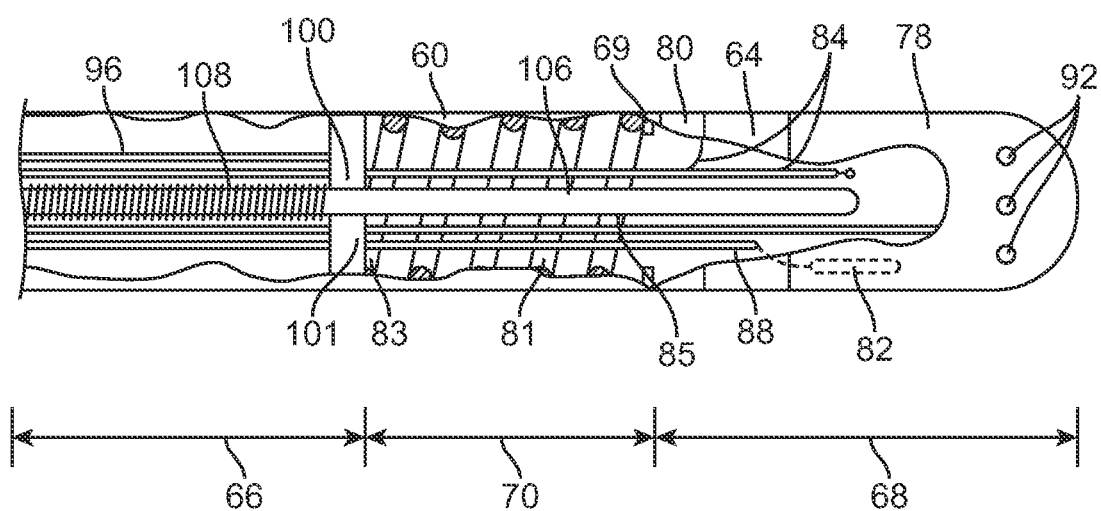
FIG. 14 is a partially cut-away perspective view of the distal end portion of an alternate embodiment of a working catheter that may be used in the robotic catheter assembly of FIG. 2, in which a flexible polymer sleeve is used instead of a bellows for the compressible section, with a spring incorporated into the compressible polymer sleeve for tensioning the push-pull dithering member.

FIG. 14 depicts an alternate embodiment of the working catheter 38 that may be used in the robotic catheter assembly of FIG. 2, in which a soft, flexible polymer sleeve is used instead of the bellows for forming the axially compressible section 70 of the catheter body 60. In particular, the compressible sleeve (which structurally coincides with the compressible section 70, and is thus referred to hereinafter by the same reference number 70) has a proximal end joined by an adhesive weld or other known method to a distal end of the bendable section 66 at a location just distal of the steering wire anchor ring 100. Similarly, a distal end of the compressible sleeve 70 is joined to the distal tip section 68 at a location just proximal of a most proximal operative element 80.

The embodiment of FIG. 14 also includes a tensioning spring 81 positioned axially within the compressible polymer sleeve 70 for tensioning the push-pull dithering member 106. In particular, a proximal end 83 of the spring 81 is compressible against a distal-facing surface 101 of the steering element anchor ring 100, which also defines a distal end of the bendable section 66. A distal end 85 of the spring 81 is compressible against a proximal-facing surface 69 of the distal tip section 68. Prior to attachment of the push-pull member 106 to the ditherer 122 (described below), the tensioning spring 81 is preferably in a relaxed, unloaded state. When initiating the instrument system for performing a procedure in a patient, the proximal end portion push pull member is retracted proximally relative to the distal tip section 68 of the catheter body 60, thereby retracting the distal tip section 68 relative to the bendable section 66, and compressing the spring 81 against the distal anchor ring surface 101. Once a specified load (e.g., approximately 80 grams in one embodiment) is reached on the push-pull member 106 (as measured by the force sensor (s) 124, described below), the proximal end portion of the push-pull member 106 is affixed to the ditherer 122, and dithering of the push-pull member 106 is commenced. The back-and-forth stroke distance traveled by the push-pull member 106 is preferably governed by maintaining the measured (or "sensed") load on the push-pull member 106 within a specified operating range, (e.g., in a range of approximately 10-50 grams, in one embodiment).

As the ditherer 122 "pushes" the push-pull member 106 and, thus, the catheter distal tip section 68 in a distal direction axially relative to the instrument driver 34 on which the ditherer 122 is mounted, the tensioning spring 81 decompresses, decreasing the sensed load on the push-pull member 106 until the lower end of the operating load range is reached, which is preferably (but not necessarily) at a point when the spring 81 returns to its unloaded state but without allowing the spring 81 to being axially tensioned. Thereafter, the ditherer 122 reverses direction and "pulls" the push-pull member 106 and, thus, the distal tip section 68 in a proximal direction axially relative to the instrument driver 34, and the spring 81 is again almost compressed against the anchor ring surface 101, resisting the inward motion of the distal tip surface 69, and increasing the measured load on the push-pull member 106 until the upper end of the load range is reached. The dithering cycle is then repeated.

It should be appreciated that the tensioning spring 81 is optional, although preferred, and that it may be used in other embodiments, such as in the embodiment of FIGS. 6 and 7, in which the compressible section comprises a bellows.

With any of the above-described embodiments, the proximal end portion of the push-pull member 106 exits from the proximal end 62 of the catheter splayer 114 and terminates at the force sensing assembly 40 mounted on the instrument driver 34. The force sensing assembly 40 generally comprises a mechanical ditherer 122 and a force sensor 124. Although only one force sensor 124 is shown and described herein, multiple force sensors can be used in alternate embodiments. In the illustrated embodiment, the ditherer 122 is mounted to the housing 110 of the instrument driver 34 proximal to the working catheter splayer 114. The ditherer 122 grasps the proximal end of the push-pull member 106 (e.g., by providing a solder ball or the like on the proximal end of the push-pull member 106), so that the push-pull members 106 can be axially dithered back and forth by the ditherer 122, thereby axially dithering the distal end tip section 64 of the catheter body 60 back and forth relative to the bendable section 66.

The length or stroke of the dithering may be adjusted depending on the nature of the procedure, but preferably is less than a few millimeters. In some embodiments, the proximal stroke of the dithering may be less than 1.5 mm. The frequency of the dithering may be several cycles per second, e.g., 2-20 Hz, thereby ensuring that any static friction is broken. It will be appreciated by those skilled in the art that some of the stroke is consumed by friction and compressibility, so the distal stroke is attenuated with respect to the proximal stroke. In some embodiments, the proximal stroke can be much reduced from 1.5 mm if the frequency goes up to near 10 Hz, since the purpose of the dithering is to keep catheter in motion.

It will be appreciated that the force sensor 124 may be disposed at various locations along the push-pull member 106, including even at the distal end 64 of the catheter body 60. In the illustrated embodiment, the force sensor 124 is disposed on the ditherer 122. The force sensor 124 is used to detect the force or load that is being applied to the distal end 64 of the catheter body 60 by detecting the force or load that is applied at the proximal end of the push-pull member 106. Thus, the force sensor 124 is able to sense the insertion and withdrawal forces applied to the distal tip 64 of the catheter body 60 via the ditherer 122. In one embodiment, the proximal end portion of the push-pull wire 106 has a crimp ball formed thereon at a proper distance, pre-set in relationship to the force sensor 124. By way of example, the crimp ball may be over molded into a block or other feature that mates with the force sensor 124.

One method for mounting the proximal portion of the push-pull member 106 on the ditherer 122 is to start with the ditherer 122 in its completed forward-stroke, allowing a slight amount of slack in the push-pull member 106. The ditherer would then be retracted distally until a predetermined load (e.g., 80 grams) is measured on the push-pull member 106. A calibration routine also may be utilized to increase the accuracy of the sensed load.

The force sensing assembly 40 may optionally comprise a strain-gage (not shown) located at the distal end of the push-pull member 106 for sensing lateral or deflection forces applied to the distal end 64 of the catheter body 60. The working catheter 38 may also comprise a sensor, e.g., an optical or capacitive sensor (not shown), located at the distal end 64 of the catheter body 60 to confirm that the distal end 64 is dithering back and forth.

Figure 8:
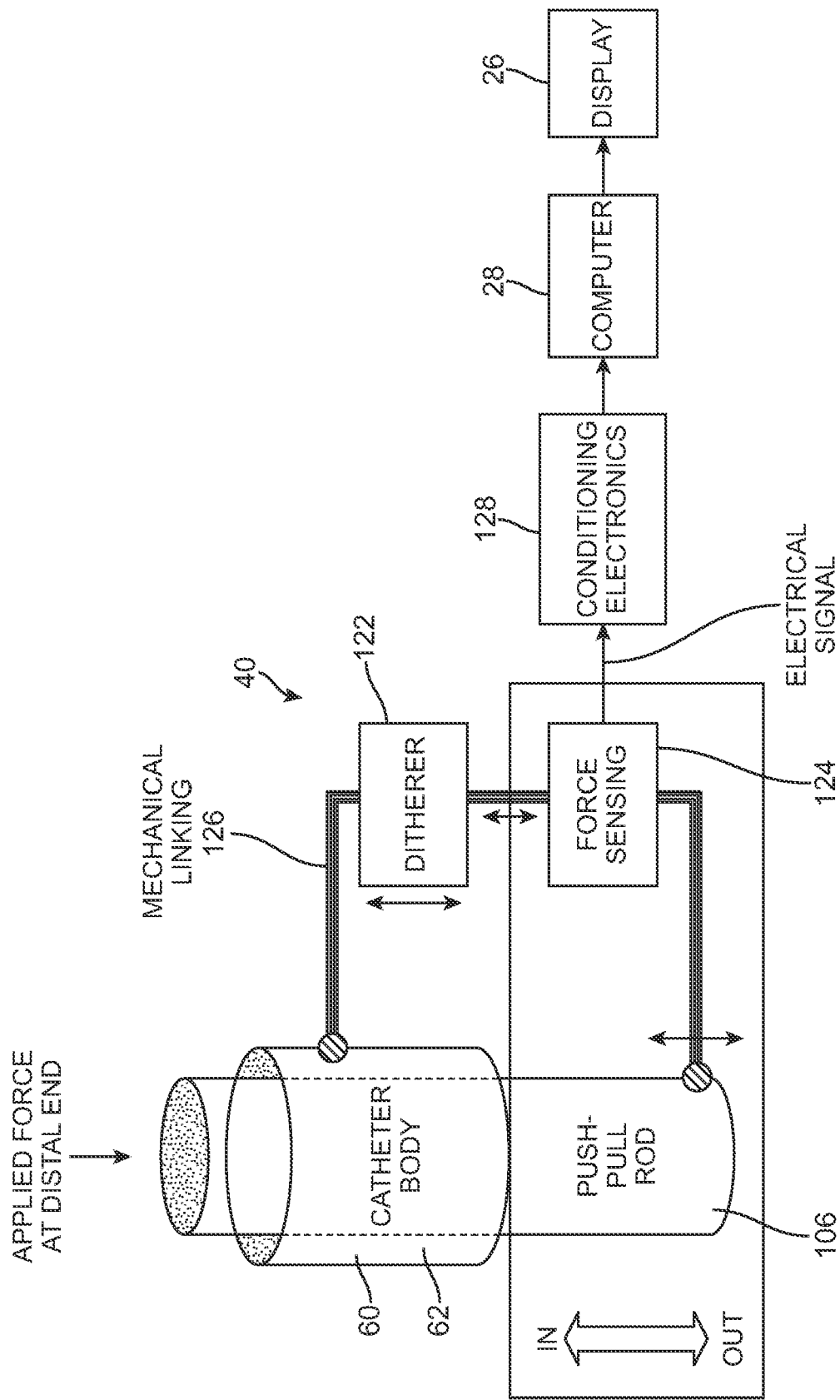
FIG. 8 is a conceptual view of a force sensing assembly used in the robotic catheter assembly of FIG. 2.

Turning now to FIG. 8, one embodiment of a force sensing assembly 40 used for measuring a force applied at the distal end 64 of the catheter body 60 will be described. In this embodiment, the distal end 64 of the catheter body 60 dithers with respect to the introducer sheath 36 and also with respect to the more proximal bendable section 66 of the working catheter 38. In order to axially dither the distal end 64 of the catheter body 60 back and forth, the ditherer 122 drives the push-pull member 106 through the force sensor 124, which measures the direct force needed to respectively insert and retract the push-pull member 106 within the lumen 104 of the working catheter 38. The ditherer 122 is mechanically grounded (via a mechanical linkage 126) and is thus, stationary relative to the proximal end 62 of the catheter body 60. So long as the introducer sheath 36 is not moved axially relative to the working catheter 38, the ditherer is also stationary relative to the introducer sheath 36. The force sensor 124 and push-pull member 106 move together relative to the proximal end 62 of the catheter body 60.

The force sensing assembly 40 is in operable communication with control station 16 via the communication link 24 for data processing. In particular, condition electronics 128 receives the electrical signals generated by the force sensor 124, and the computer 28 processes the conditioned electrical signals. A representation of the axial force applied at the distal end 64 of the catheter body 60 can be displayed on the monitor 26.

Over one or more dithering cycles, the force profiles or waveforms obtained from the force signals can be used to accurately estimate the contact forces at the distal end 64 of the catheter body 60. In particular, the computer 28 obtains a baseline force measurement by receiving signals from force sensor 124 when the push-pull member 106 is dithered back and forth at a time that no external axial force is being applied to the distal end 64 of the catheter body 60. The computer 28 may then later obtain a total force measurement by receiving signals from the force sensor 124 when the push-pull member 106 is dithered back and forth and an external axial force is applied to the distal end 64 of the catheter body 60 (e.g., when the distal tip of the catheter 38 contacts tissue). The computer 28 then computes the external axial force applied to the distal end 64 of the catheter body 60 by subtracting the baseline force measurement from the total force measurement. Notably, the total force measurement may capture signal induced by physiological cycles, such as the respiratory cycle and heart cycle. To interpret this signal, such as for control purposes, the force sensing assembly 40 may comprise a filter (not shown) for separating the physiological variations within the total force measurement.

Further details on this type of force sensor system, along with various other embodiments of dithering force sensor assemblies, are provided in U.S. patent application Ser. No. 11/678,001, which has previously been incorporated herein by reference.

It will be appreciated that, as the working catheter 38 is articulated (bent) during a procedure, the catheter body 60 compresses. Additionally there are geometric displacements on the catheter body 60, as well as on the push-pull member 106 if it is located off the neutral axis of the catheter shaft. Both of these displacements may be calculated and compensated for by the varying the stroke length of the ditherer 122 during operation. This compensation eliminates the forces generated by the articulation of the catheter body 60 to be translated to the force sensor 124.

Figure 16:
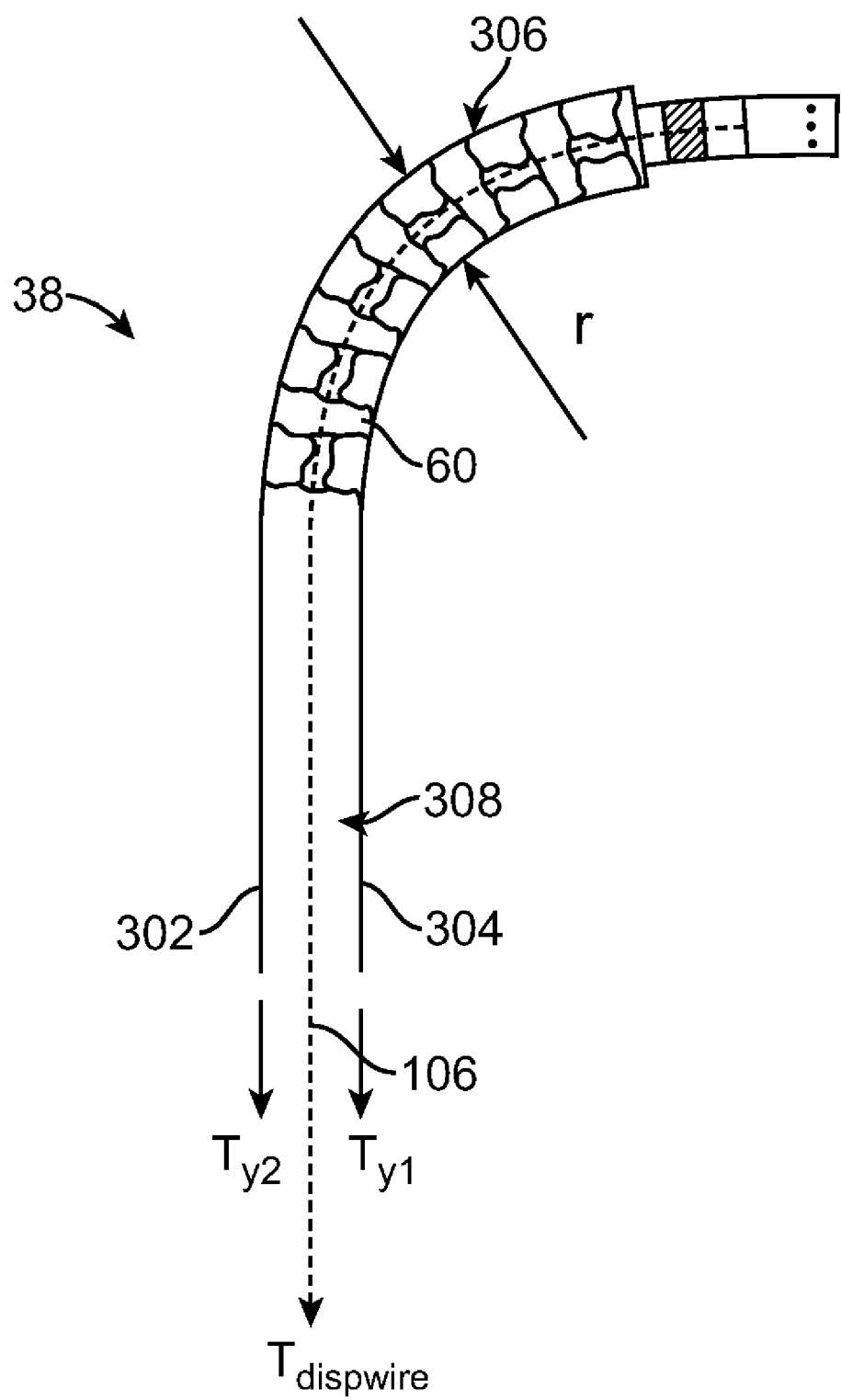
FIG. 16 is a side view of the catheter as it is bent in one direction.
Figure 17:
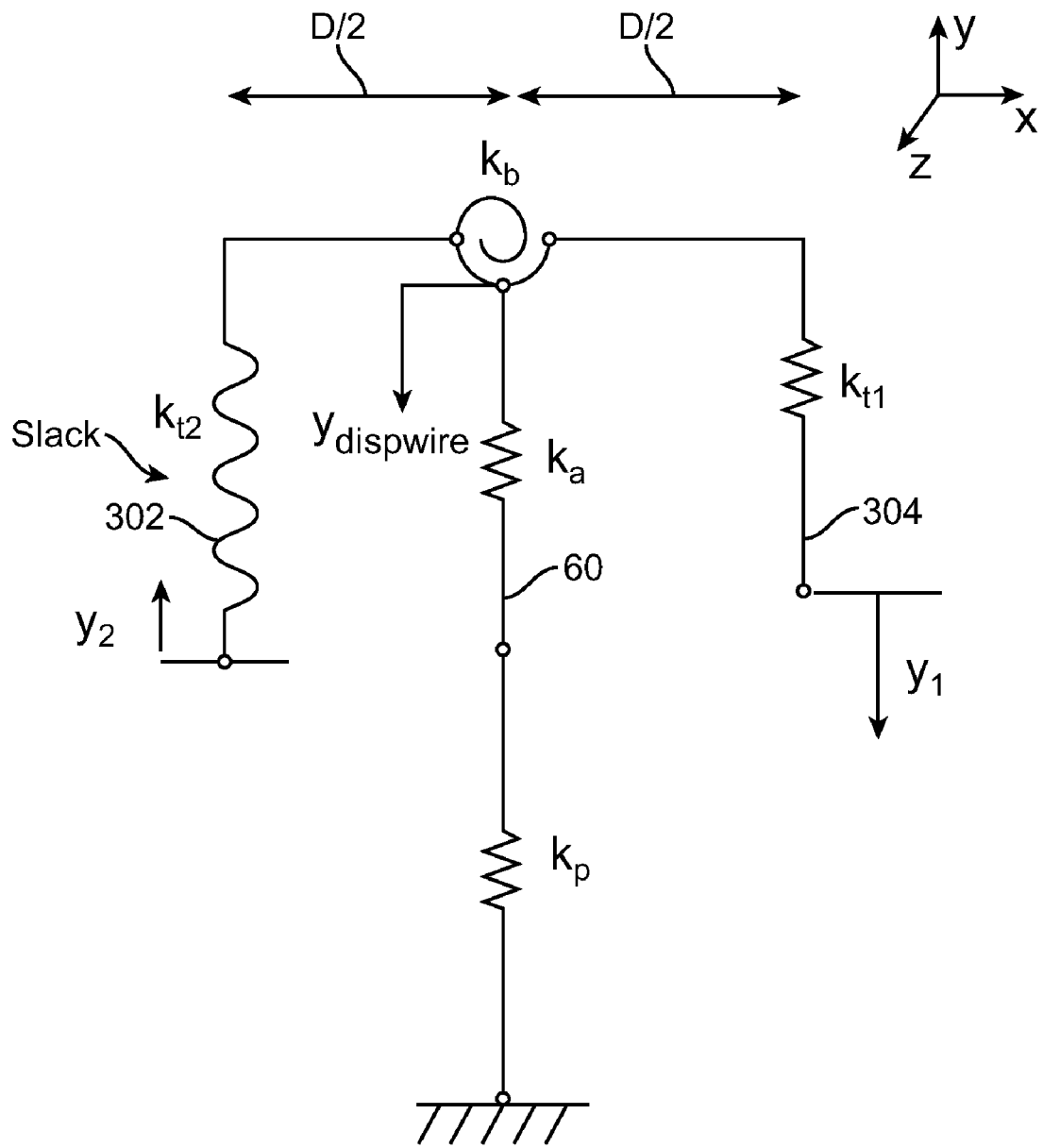
FIG. 17 depicts a model of the forces applied to a catheter as it is articulated which treats the catheter and each tendon member as springs with different spring constants depending on their stiffness.

With reference to FIGS. 16 and 17, the compensation mathematics involved with the mechanics of the working catheter 38 and push-pull member 106 for one exemplary embodiment will now be described, including the variables that contribute to the tension of the push-pull member 106 when the catheter 38 is articulated. As seen in FIG. 16, the catheter may have steering control elements or tendons 302, 304 and an articulation section 306 and a non-articulating section 308 each with different stiffness. The radius of curvature defining the amount of bend in the catheter is represented by r. FIG. 17 depicts a model of the forces applied to a catheter as it is articulated which treats the catheter and each tendon member as springs with different spring constants depending on their stiffness. Since the articulation section varies in stiffness from the proximal section, the axial stiffness of the catheter body 60 or stiffness in compression is represented as two different spring constants $k_a$ and $k_p$. The catheter also has stiffness in bending which is represented by the spring constant $k_b$. Each of the tendons 302, 304 also has a stiffness $k_{t2}$ and $k_{t1}$ respectively. The tendons 302, 304 are shown offset from the center of the catheter by half the diameter of the catheter d/2.

To articulate the catheter, the tendons 302, 304 are displaced by a distance $y_2$ and $y_1$ respectively. In this model, a negative y displacement will place a tendon in tension T while a positive y displacement will place the tendon in slack or zero tension. When in a straight configuration, the tension in each tendon $T_{y1}$ and $T_{y2}$ are equal. In order to bend the catheter (as shown in FIG. 16), one tendon 304 is placed tension $T_{y1}$ in while the other tendon 302 is given slack $T_{y2}=0$. The push pull member (shown as a displacement wire) 106 is also shown running down the central axis and its displacement is shown as $y_{dispwire}$.

The moments about the y and x axis will be 0 but in bending the moments about the z axis can be calculated as follows:

$$\Sigma M = T_{y1}(d/2) = k_b(1/r) \quad (1)$$

Solving for $T_{y1}$ we get:

$$T_{y1} = 2k_b/Dr \quad (2)$$

Summing the tension in the system using Hooke's law T=kx, we get:

$$T_{dispwire} + T_{y1} = k_a(\Delta L_d/L_a) + k_p(\Delta L_p/L_p) + k_{t1}(\Delta L_t/L_t) \quad (3)$$

Plugging equation 2 into equation 3 for $T_{y1}$ then solving for Tdispwire gives:

$$T_{dispwire} + 2k_b/Dr = k_a(\Delta L_d/L_a) + k_p(\Delta L_p/L_p) + k_{t1}(\Delta L_t/L_t) \quad (4)$$

$$T_{dispwire} = k_a(\Delta L_d/L_a) + k_p(\Delta L_p/L_p) + k_{t1}(\Delta L_t/L_t) + (-2k_b/Dr) \quad (5)$$

Figure 18:
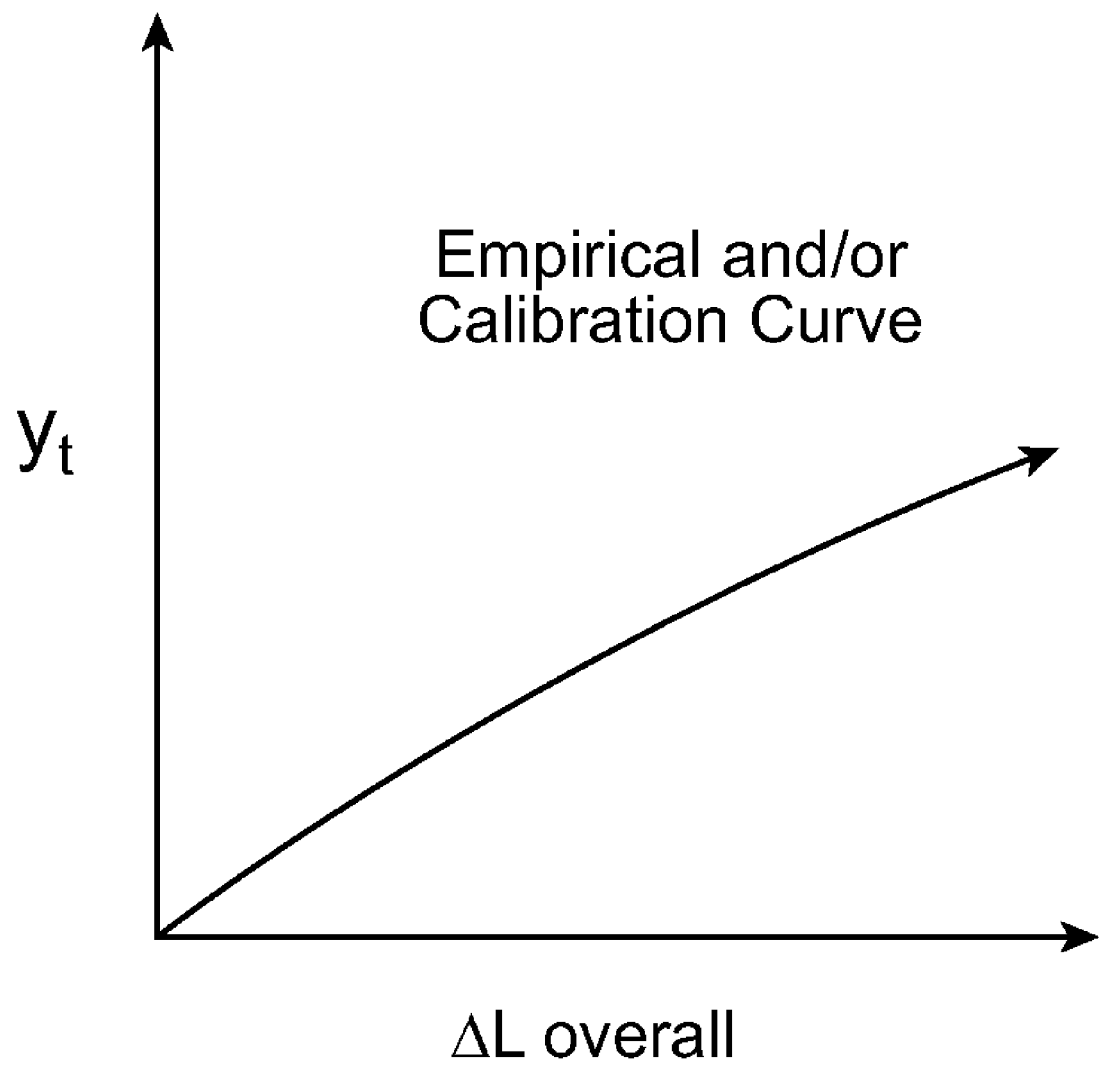
FIG. 18 is a graph of displacement of the guide tendon vs. the overall strain (or change in length) of the shaft.

Equation 5 shows that, during articulation, the catheter body 60 compresses by a $\Delta L$ for a given radius. In order for the tension of the push-pull member 106 to remain constant during articulation, the member 106 must also move by $\Delta L$ by the ditherer 122 (shown in FIG. 3). $\Delta L$ may be determined through analytical and/or empirical methods. In equation 5 above the known physical constants are the spring constants (ka, kp, kt, kb), the catheter diameter (D), and the catheter lengths (La, Lp, Lt). The radius of curvature r would be a user input. Thus, $\Delta L$ can be measured empirically for various points of r to create a table that can be used to determine the dither stroke necessary to keep the tension in the displacement wire constant during bending. The table could be used to create a graph of displacement of the guide tendon vs. the overall strain of the shaft (or change in length of the shaft) as shown in FIG. 18. The graph can then be used analytically to determine $\Delta L$ with respect to tendon displacement.

Figure 9A:
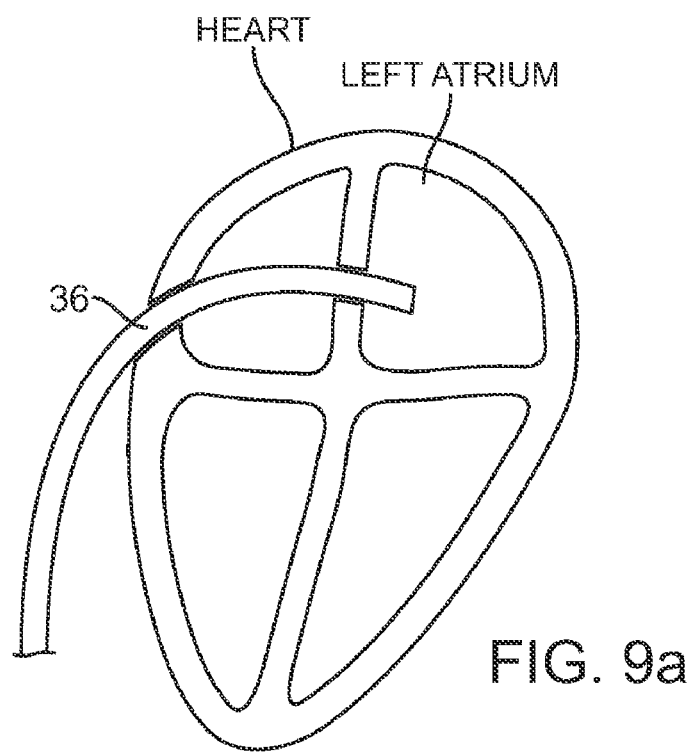
FIGS. 9a-d illustrates a method of operating the robotic catheter system of FIG. 1 to sense a force applied between endocardial tissue and the distal end of the working catheter illustrated in FIG. 6.
Figure 9B:
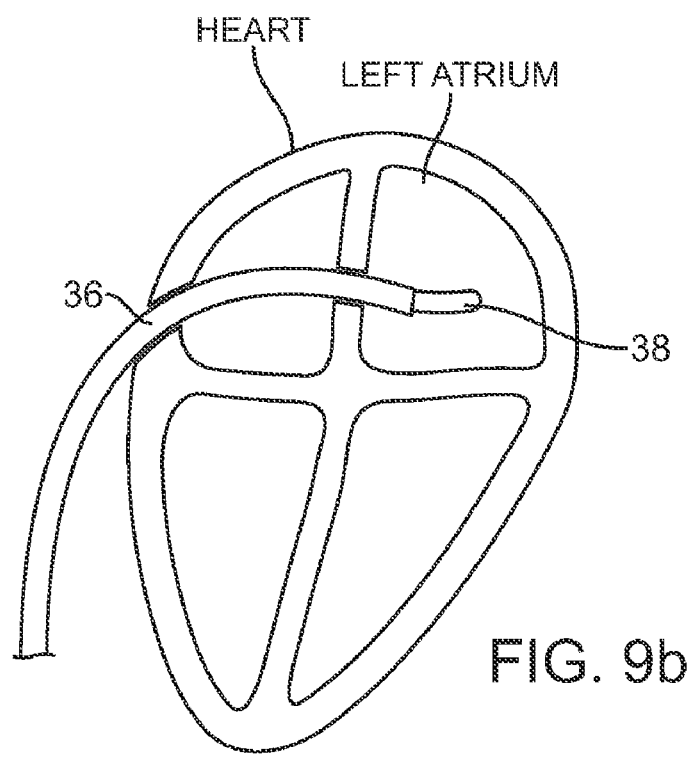

Having described the robotic catheter system 10, an exemplary method of using the robotic catheter system 10 to perform therapeutic and/or diagnostic functions on a patient will now be described. First, the introducer sheath 36, with the working catheter 38 retracted therein, is intravascularly introduced through a puncture within the patient's body and robotically advanced/maneuvered through the vasculature of the patient to a target site, such as a chamber of the heart, as illustrated in FIG. 9a. In this case, the introducer sheath 36 is transeptally introduced into the left atrium of the heart. The working catheter 38 is then robotically advanced out of the introducer sheath 36, as shown in FIG. 9b. The distal end of the working catheter 38 is then axially dithered back and forth relative to the proximal end of the working catheter 38, as shown by the arrows in FIG. 9c. In the illustrated embodiment, this is accomplished by operating the ditherer 122 to axially dither the push-pull member 106 back and forth, thereby dithering the distal end of the working catheter 38 back and forth via operation of the bellows or alternatively designed compressible section 70.

Figure 9C:
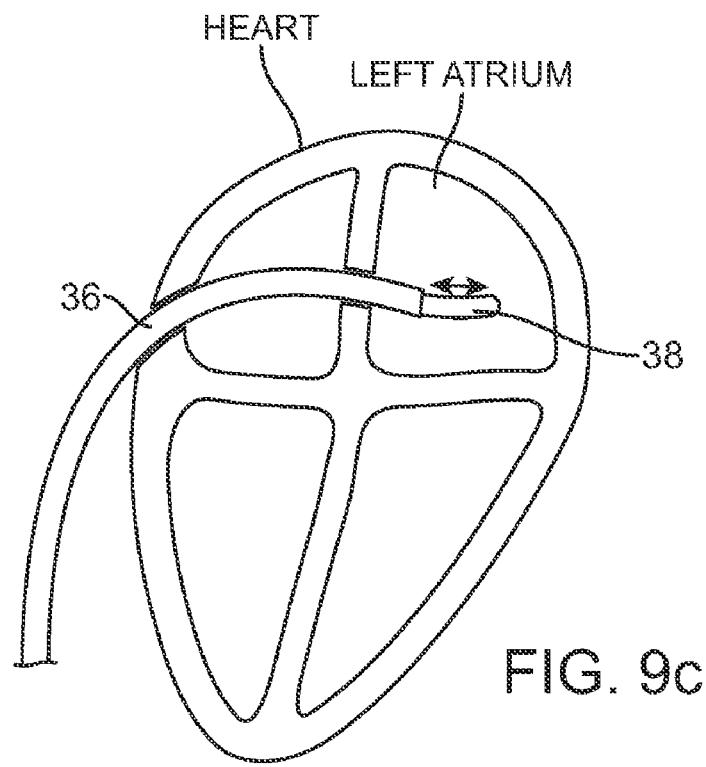
Figure 9D:
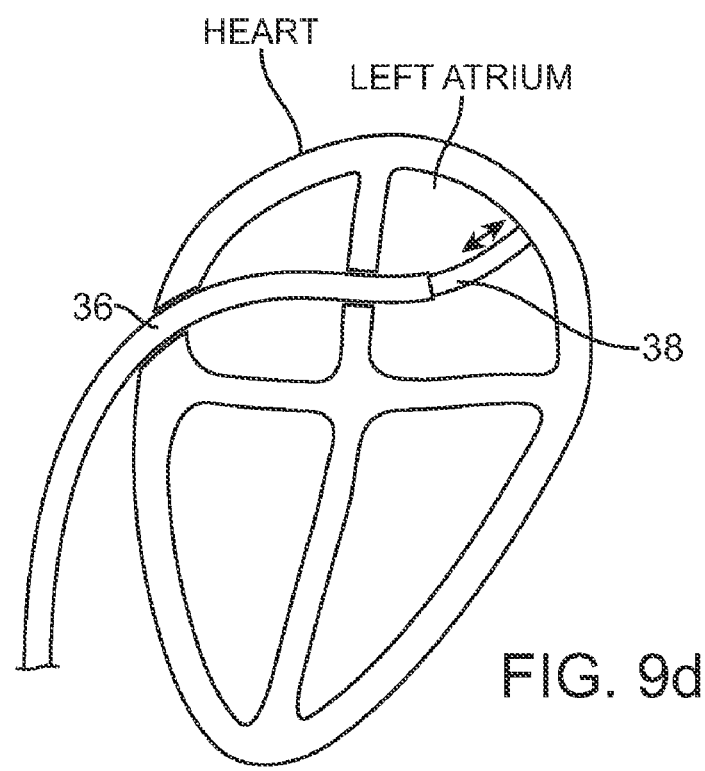

Preferably, as shown in FIG. 9c, the distal end of the working catheter 38 is axially dithered back and forth when an external axial force is not presently applied between the tissue and the distal end of the working catheter 38, and measuring the force at the force sensor 124 to obtain a baseline force measurement. While the distal end of the working catheter 38 is being dithered, it is robotically moved within at least one-degree of freedom (e.g., by deflecting the distal end of the working catheter 38), thereby placing its distal tip section 64 in contact with tissue, as shown in FIG. 9d. Because the force at the force sensor 124 is continuously measured, the total force measurement will be obtained as the distal end of the working catheter 38 is placed into contact with the tissue. The axial force applied between the tissue and the distal end of the working catheter 38 can then be computed (in this case, by the computer 28) by subtracting the baseline force measurement from the total force measurement.

The operative elements at the distal end of the working catheter 38 (in this case, the tip ablation electrode 78 and mapping ring electrode 80) can then be operated to perform the therapeutic and/or diagnostic function (in this case, tissue ablation and/or mapping) on the patient. The distal end of the working catheter 38 can be moved to a different region on the tissue. The axial force applied between the tissue and the distal end of the working catheter 38 can again then be measured and the operative elements at the distal end of the working catheter 38 operated to again perform the therapeutic and/or diagnostic function.

Figure 10:
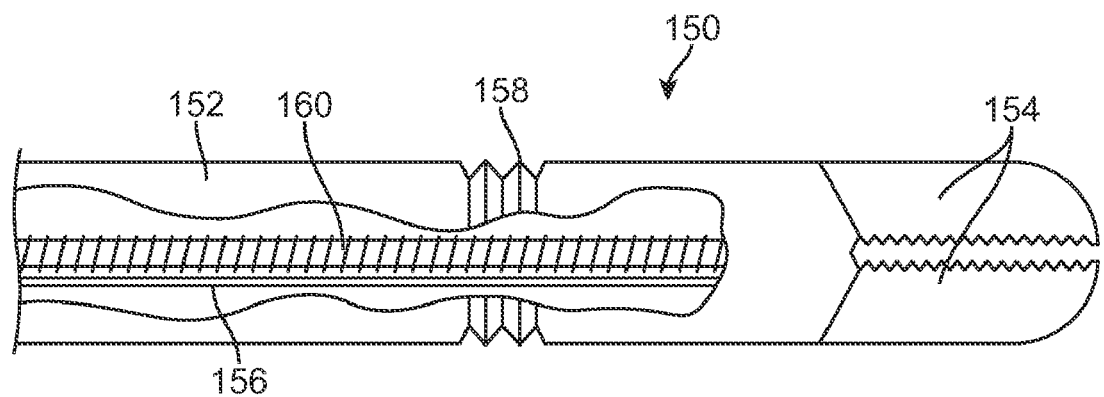
FIG. 10 is a plan view of the distal end of an alternate working catheter that may be used in the robotic catheter assembly of FIG. 2.

As briefly discussed above, the force sensing mechanism disclosed herein and be used with medical devices with operative elements other than ablation/mapping electrodes. For example, operative elements, such as energy delivering laser fibers, scalpel, grasper/tweezers; sensor (radiometer, IR, spectrometer (excitation light source in combination with a detector)), etc., can be used. For example, FIG. 10 illustrates a robotically controlled working catheter 150 having an elongated catheter body 152, a pair of grasper arms 154 affixed to the distal end of the catheter body 152, and a cable 156 extending through the catheter body 152 and coupled to the grasper arms 154.

The grasper arms 154 can be spring-loaded to open relative to each other, in which case, the cable 156 can be pulled to close the arms 154 relative to each other. As with the working catheter 38, the working catheter 150 includes an axially flexible section 158, and a push-pull member 160 slidably disposed within a central lumen 162 extending through the catheter body 152. The distal end of the push-pull member 160 is affixed to the catheter body 152 at a point distal to the axially flexible section 158, and in particular, to the distal end of the catheter body 150, and a proximal end that extends out from the proximal end of the catheter body 152, so that it can be suitably coupled to the force sensing assembly 40 in the manner discussed above. As with the catheter 38, the catheter 150 optionally comprises a centering coil 162 affixed around the push-pull member 160.

Figure 11:
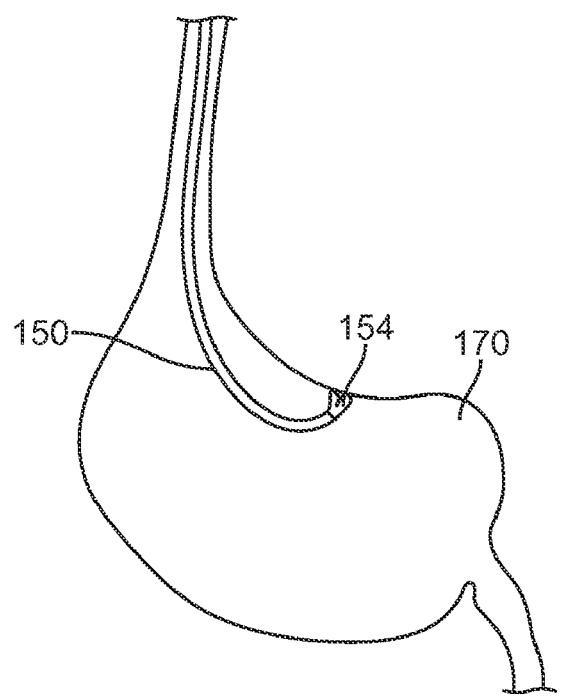
FIG. 11 illustrates a method of operating the robotic catheter system of FIG. 1 to sense a force applied between the inner lining of a stomach and the distal end of the working catheter illustrated in FIG. 10.

The force sensing mechanism disclosed herein can be used to perform medical procedures in anatomical regions other than the heart. For example, as shown in FIG. 11, the working catheter 150 can be used to perform a surgical procedure within the cavity of the stomach 170 while sensing the force between the grasper arms 154 and the wall of the stomach to prevent perforation of the inner lining of the stomach.

It will be appreciated that there must be adequate slack in the fluid supply tube 94 to allow for the distal tip section 64 to be dithered relative to the bendable section 66 without tensioning and/or compressing the fluid supply tube 94. Further, the fluid supply tube 94 must be sufficiently flexible, and preferably have a low friction, e.g., coated, exterior surface in order to minimize internal frictional forces within the catheter lumen 104 created by its presence. This is particularly important since the fluid supply tube 94 is "dithered" along with the distal tip section 64 to which it is attached relative to the rest of the catheter body 60. For example, the fluid supply tube 94 may be provided with a service loop (not shown) or its own bellows (not shown) within the interior of axially compressible section 70 of the catheter body 60. However, such features necessarily take up space and may be difficult to implement without interfering with the push-pull member 106. Such features may also result in an irregular amount of fluid being delivered out the ports 92 and/or add undesirable stiffness to the axially compressible section 70.

Figure 15A:
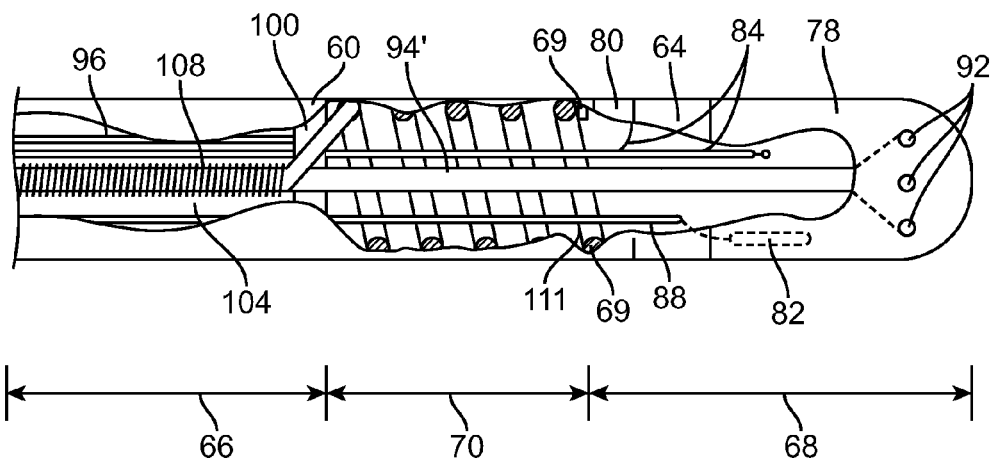
FIGS. 15a and 15b are partially cut-away perspective views of the respective distal and proximal end portions of still another embodiment of a working catheter that may be used in the robotic catheter assembly of FIG. 2, in which a fluid supply tube used to supply cooling fluid to the distal tip of the catheter is also used as a push-pull member for dithering the distal tip of the catheter, and in which a distal end portion of an axial stiffening coil formed as a spring polymer sleeve section.
Figure 15B:
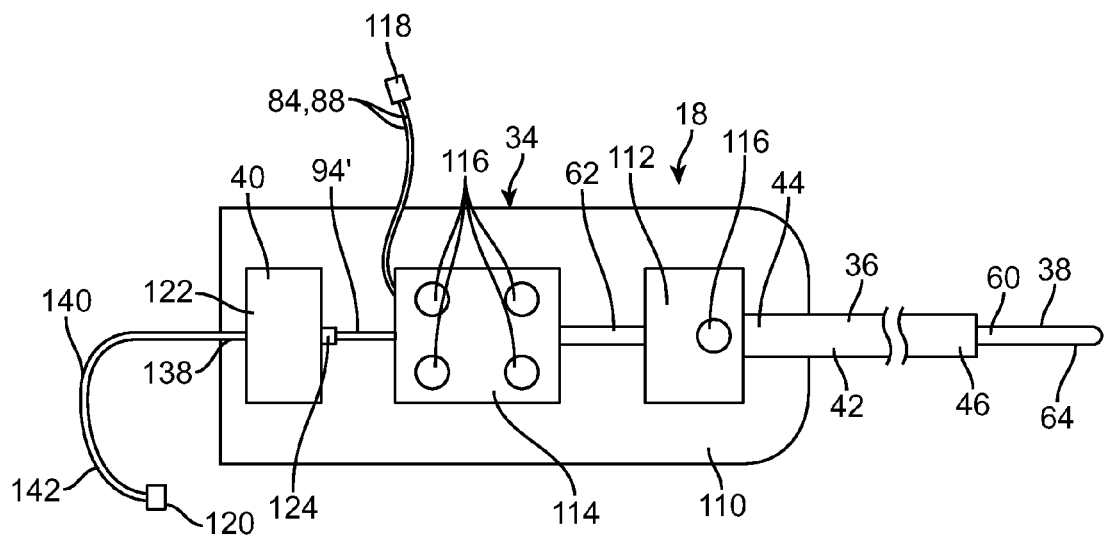

In yet another alternate embodiment of the working catheter 38, shown in FIGS. 15a and 15b, these issues are resolved by using the cooling fluid supply tube (designated 94') as the push-pull member for dithering the distal end section 68 relative to the bendable section 66. In particular, the fluid supply tube 94' is extended down the center of the working catheter central lumen 104, and (as depicted in FIG. 15a) down the axial lumen of an (optional) stiffening coil 108, through the steering wire anchor ring 100, and then through the compressible section (e.g., a flexible polymer sleeve) 70 of the catheter body 60 to the distal tip section 68.

As mentioned above, a distal end portion 111 of the stiffening coil 108 extends through the open center of the steering wire anchor ring 100, and through the axially compressible section 70, before terminating against a proximal end surface 69 of the distal tip section 68. In particular, in the distal portion 111 of the stiffening coil 108, the pitch of the individual coil windings is significantly opened, and the diameter of the individual windings is substantially expanded, so that the coil portion 111 functions as a resilient tensioning spring to help maintain the fluid supply tube 94' in tension during the dithering operation, much in the same manner as the tensioning spring 81 maintains the push-pull member 106 in tension in the above-described embodiment of FIG. 14.

As seen in FIG. 15b, a proximal end portion 138 of the fluid supply tube 94' extends out the proximal end of the working catheter 38 and may be mechanically coupled (e.g., grasped by) the ditherer 122 in essentially the same manner as the push-pull member 106 in above-described embodiments, except that some accommodation may be needed in order to not "pinch" the fluid supply tube 94' in a manner that restricts fluid flow there through. A service loop 140 is provided in a still more proximal portion 142 of the fluid supply tube 94' extending proximally of the ditherer 122 to provide slack needed for the fluid supply tube 94' to be used as the push-pull dithering member. The fluid supply tube 94' is otherwise connected to a fluid source in a similar manner as fluid supply tube 94 in the previously described embodiments. As with the tensioning spring 81 in the embodiment of FIG. 14, the distal portion 111 of the stiffening spring 108 is preferably in an unloaded state prior to attachment of the fluid delivery tube 94' to the mechanical ditherer 122.

Thus, the working catheter 38' of FIGS. 15a and 15b provides for axial dithering of the distal tip section 64 relative to the bendable section 66, while still providing a fluid supply for open irrigation in the body. The fluid delivery tube 94' is preferably stiff, just like the push-pull wire 106 of the previously described embodiments, and is also preferably kept in tension by the distal portion 111 of the stiffening coil 108. Advantageously, no stress relief bellows or service loop is needed along the distal portion of the fluid supply tube 94' to allow for the dithering operation.

Although the previous embodiments of the working catheter 38 have axially compressible section, such as a compressible polymer sleeve or a bellows, with or without an additional spring member for tensioning the push-pull member, in order that the distal tip section can be axially displaced relative to the remaining portion of the catheter body, an "axially translatable" section can be used in alternate embodiments to perform this function.

Figure 12:
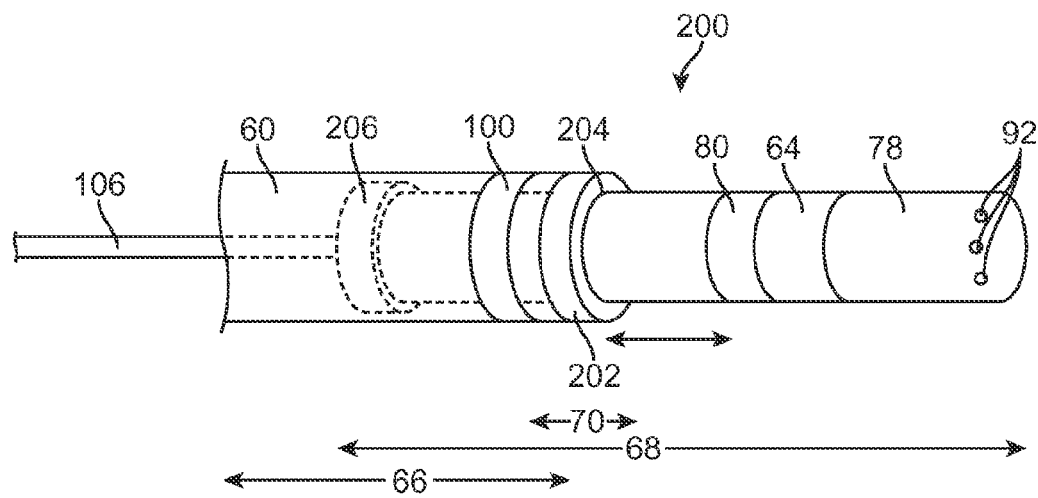
FIG. 12 is a perspective view of the distal end of still another working catheter that may be used in the robotic catheter assembly of FIG. 2.

For example, referring to FIG. 12, a working catheter 200 is similar to the above-described working catheter 38', with the exception that instead of an axially compressible section 70 (e.g., a compressible polymer sleeve or bellows), the working catheter 200 includes an axially translatable section (designated 70') that has a seal 202 suitably mounted to the distal end of the bendable shaft section 66. The seal 202 includes an annular aperture 204 through which the distal tip section 68 is disposed. The diameter of the aperture 204 is equal to or less than the outer diameter of the distal tip section 68. Thus, the distal tip section 68 is slidably disposed within the more proximal bendable shaft section 66 via the seal 202, which prevents bodily fluids, such as blood, from entering the working catheter 200 via the interface between the respective catheter shaft sections 66, 68. The distal end of the push-pull member 106 is affixed to the distal tip section 68, and thus, is displaced with the distal tip section 68 in the manner and with the result described above with respect to the working catheter 38.

The seal 200 may be composed of a suitable material, such as rubber, to allow the respective bendable and distal tip sections 66, 68 to easily slide relative to the each other while maintaining a good seal therebetween. The proximal end of the distal tip section 68 preferably includes an annular flange 206 that abuts the seal 202 during the farthest extent of distal tip section 68, thereby preventing the distal tip section 68 from disengaging from the bendable shaft section 66. In alternative embodiments, the seal 202 is suitably mounted to the proximal end of the distal tip section 68, in which case, the bendable shaft section 66 will be slidably disposed within the distal tip section 68 via the seal 202.

Figure 13:
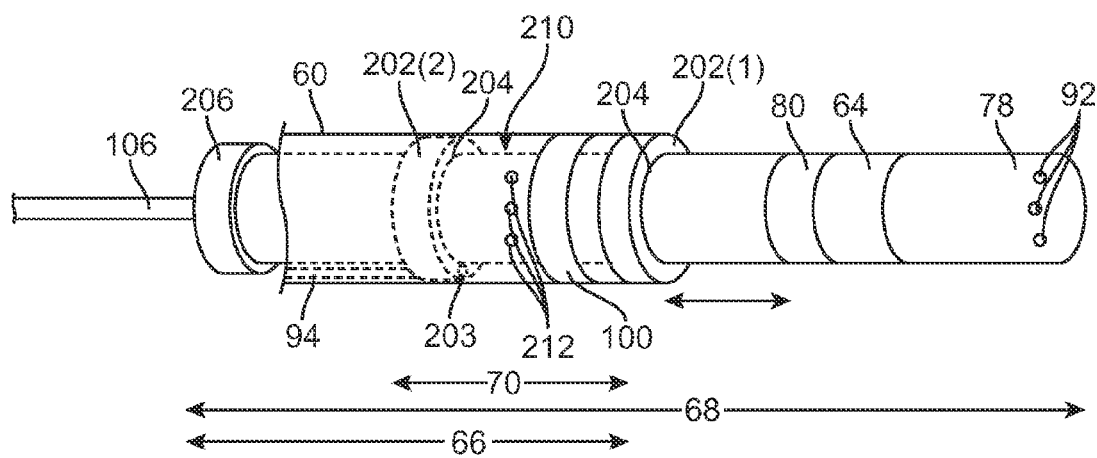
FIG. 13 is a perspective view of the distal end of yet another working catheter that may be used in the robotic catheter assembly of FIG. 2.

In another alternative embodiment illustrated in FIG. 13, the working catheter 200 includes a pair of seals 202—one seal 202(1) mounted to the distal end of the bendable shaft section 66, and another seal 202(2) mounted within the bendable shaft section 66 proximal to the first seal 202(1). Each of the seals 202 includes an annular aperture 204 through which the distal tip section 68 is disposed. Thus, the seals 202 provide suitable bearing surfaces that maintain axial alignment of the distal tip section 68 within the bendable shaft section 66. In this embodiment, the distal end of a fluid tube 94 extending through the catheter body 60 terminates in an aperture 208 within the proximal seal 202(2). Thus, fluid can be conveyed into a chamber 210 formed between the seals 202, thereby creating a positive pressure therein. As a result, any bodily fluids, such as blood, that would otherwise leak through the distal seal 202(1) is prevented from entering the working catheter 200 due to the positive pressure. Furthermore, apertures 212 are formed in the distal tip section 68 through which the positively pressurized fluid can be conveyed to the irrigation ports 92 on the electrode 78 to provide the irrigation function described above.

While multiple embodiments and variations of the many aspects of the invention have been disclosed and described herein, such disclosure is provided for purposes of illustration only. Many combinations and permutations of the disclosed system are useful in minimally invasive surgery, and the system is configured to be flexible. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, it should be understood that the invention generally, as well as the specific embodiments described herein, are not limited to the particular forms or methods disclosed, but also cover all modifications, equivalents and alternatives falling within the scope of the appended claims.

What is claimed is:

1. A method for sensing force on a robotically controlled medical instrument, the method comprising:

introducing a medical probe into a patient, the medical probe having an elongated probe body comprising a central lumen, and a push-pull member extending axially through the central lumen, a distal end of the push-pull member being attached to a distal end portion of the probe body;

mechanically displacing a proximal end of the push-pull member back and forth in a cyclical manner without any external force applied to the distal end portion of the probe body;

mechanically displacing the proximal end of the push-pull member back and forth in a cyclical manner with external force axially applied between internal body tissue of the patient and the distal end portion of the probe body; and determining the external force applied between the internal body tissue of the patient and the distal end portion of the probe body, wherein the external force applied between the internal body tissue of the patient and the distal end portion of the probe body is determined by obtaining a baseline force measurement when the distal end portion of the probe body is axially dithered back and forth without any external axial force applied to the distal end portion of the probe body, obtaining a total force measurement when the distal end portion of the probe body is dithered back and forth with the external axial force axially applied between the tissue and the distal end portion of the probe body, and subtracting the baseline force measurement from the total force measurement.

2. The medical method of claim 1, the probe body further comprising an axially variable-length portion interposed between the respective distal end and more proximal portions of the probe body.

3. The medical method of claim 2, wherein the push-pull member comprises a fluid delivery tube having an open distal end coupled to the distal end portion of the probe body.

4. The medical method of claim 2, wherein the axially variable-length portion of the probe body comprises a spring.

5. The medical method of claim 2, wherein the probe body is robotically controlled by an instrument driver having an adapter configured to be operatively coupled to one or more steering wires extending through the probe body for controllable bending of a bendable portion of the probe body in at least one direction, the one or more steering wires having distal ends affixed to the probe body at a steering wire anchor member located at a distal end of the bendable portion, the push-pull member extending distally past the anchor member to the distal end portion of the probe body.

* * * * *